United States Patent [19]

Evans et al.

[11] Patent Number: 5,532,206
[45] Date of Patent: Jul. 2, 1996

[54] METHOD OF TREATING PLANTS OR PLANT TISSUES WITH C-16,17-DIHYDRO GIBBERELLINS

[76] Inventors: Lloyd T. Evans, 3 Elliot Street, Campbell, Australian Capital Territory, 2600; Roderick W. King, 33 Norman Street, Deakin, Australian Capital Territory, 2600; Lewis N. Mander, 15 Juwin Street, Aranda, Australian Capital Territory, 2614, all of Australia; David W. Pearce, 1325 17th Avenue South, Lethbridge, Alberta, T1K 1A3; Richard P. Pharis, RR2, Box 609, Cochrane, Alberta, T0L 0W0, both of Canada

[21] Appl. No.: 196,251

[22] PCT Filed: Aug. 14, 1992

[86] PCT No.: PCT/AU92/00426

§ 371 Date: May 12, 1994

§ 102(e) Date: May 12, 1994

[87] PCT Pub. No.: WO93/03616

PCT Pub. Date: Mar. 4, 1993

[30] Foreign Application Priority Data

Aug. 15, 1991 [GB] United Kingdom ............ 9117634

[51] Int. Cl.$^6$ .......... A01N 37/08; A01N 43/08; A01N 45/00
[52] U.S. Cl. .......... 504/176; 504/182; 504/299; 504/320; 504/348; 504/353
[58] Field of Search ............ 504/299, 320, 504/348, 353, 176, 182

[56] References Cited

PUBLICATIONS

Crozier et al "The biological activity of 26 gibberrellins . . ." *Can. J. of Bot.* 48: 867–877. 1970.

Phinney et al "Dwarf Mutants in Maize—The Gibberrellin Biosynthetic Pathway" in M. Bopp, ed. *Plant Growth Substances* 1985.

Sponsel, V. "Gibberellin Biosynthesis and Metabolism", in P. Davies, ed. *Plant Hormones and their Role in Plant Growth and Development.* 1987.

Mander, L. "The Chemistry of Gibberellins: an Overview" *Chem Rev.* 92: 573–612. 1992.

*Primary Examiner*—S. Mark Clardy
*Attorney, Agent, or Firm*—Birch, Stewart, Kolasch & Birch

[57] ABSTRACT

A method is provided for treating plants or plant tissues (including cuttings, roots, bulbs, corns, tubers, rhizomes and seeds) in order to induce a desired tissue morphology and/or a desired physiological state by applying to the plant an amount of a C-16,17-dihydro gibberellin or C-16,17-dihydro gibberellin precursor effective to produce an at least partial inhibition of the formation of effector gibberellins in said plant.

Effects obtainable include dwarfing, stem and shoot and/or root (radicle) growth retardation, flowering, improved fruit quality, inhibiting fruit ripening, improving fruit set, controlling weed growth, inducing male sterility, retarded bud break and tillering.

59 Claims, 28 Drawing Sheets

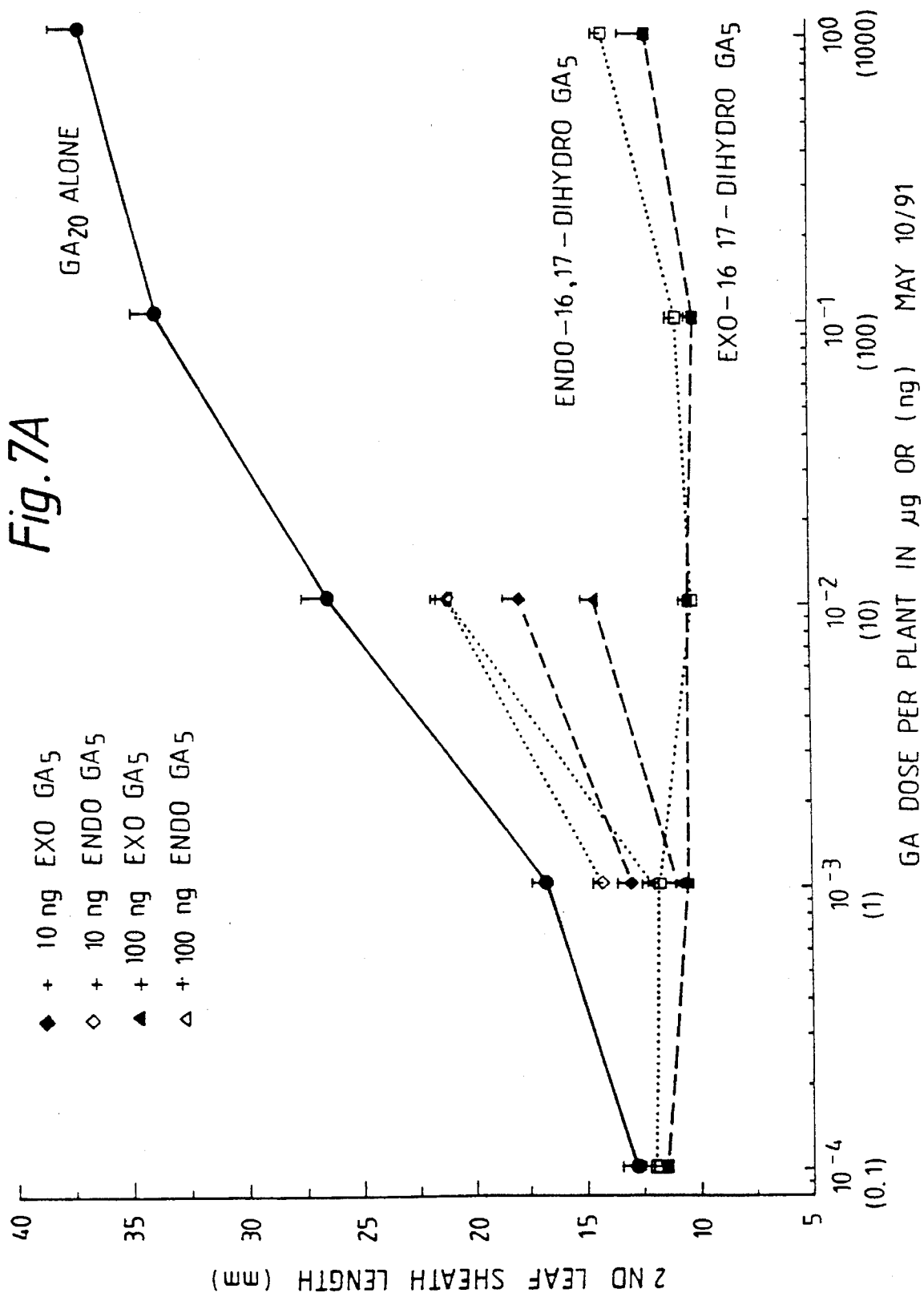

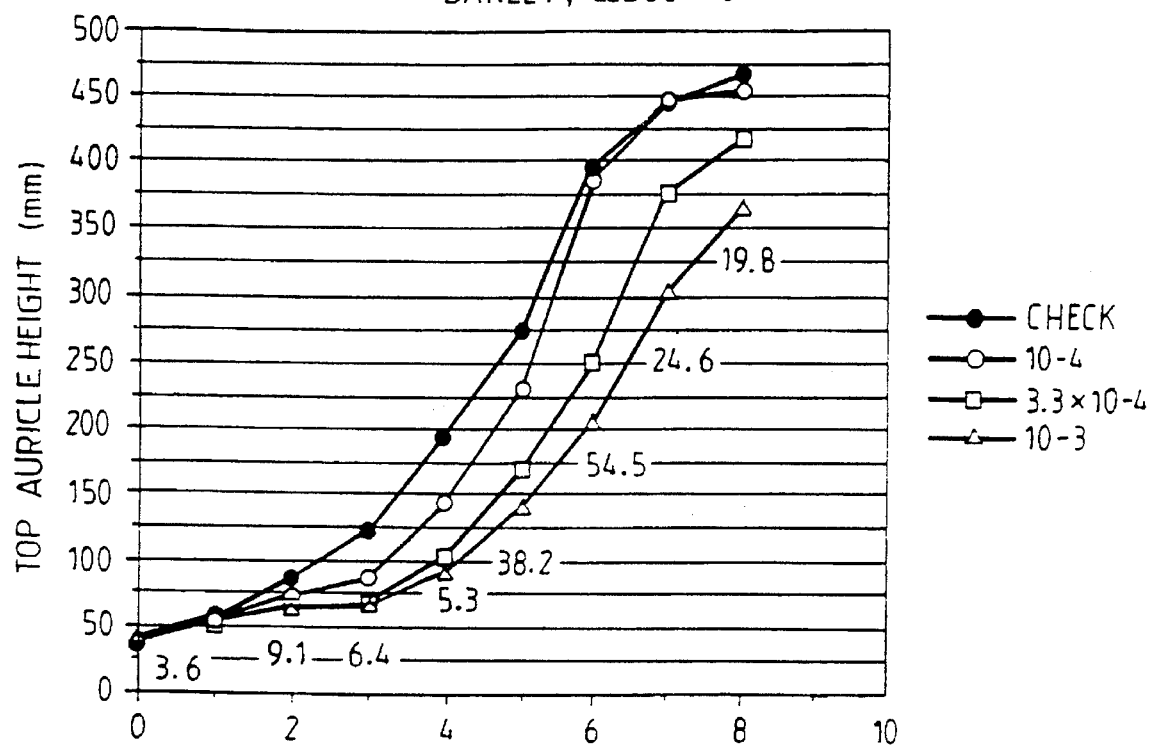
Fig. 21  3 × SPRAY OF EXO-DIHYDRO GA$_5$
BARLEY, LEDUC × 3
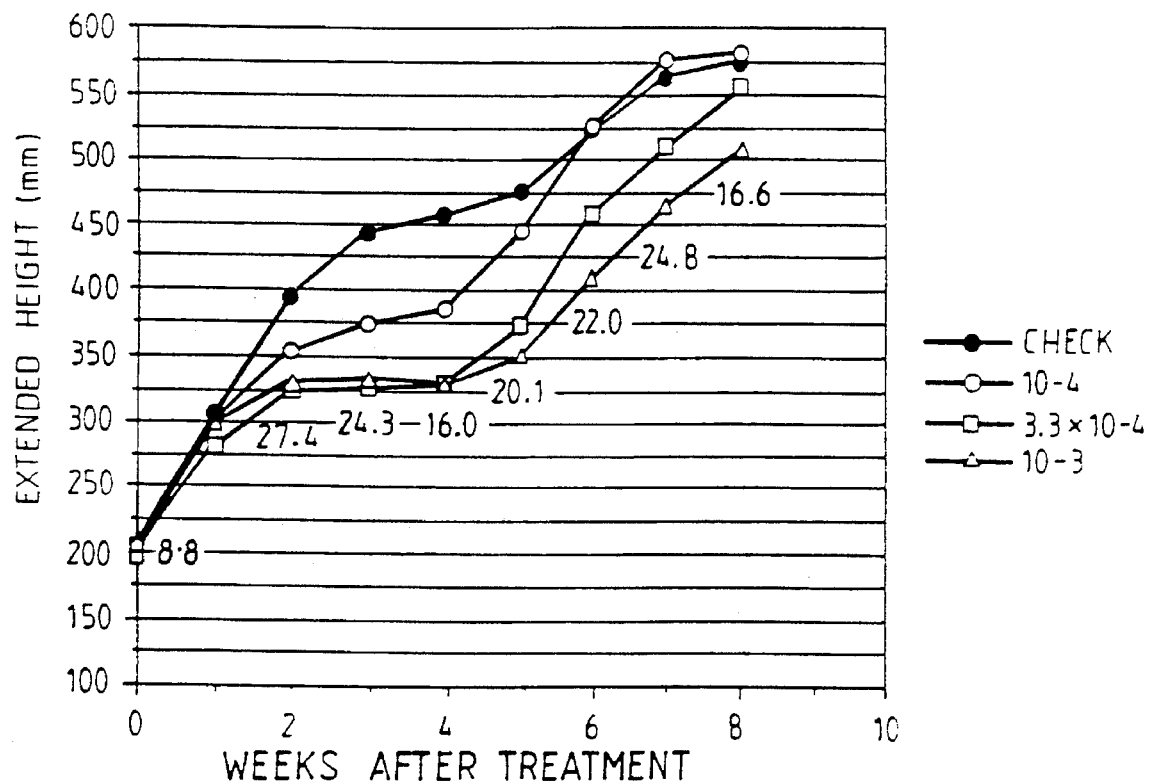
Fig. 22
WEEKS AFTER TREATMENT

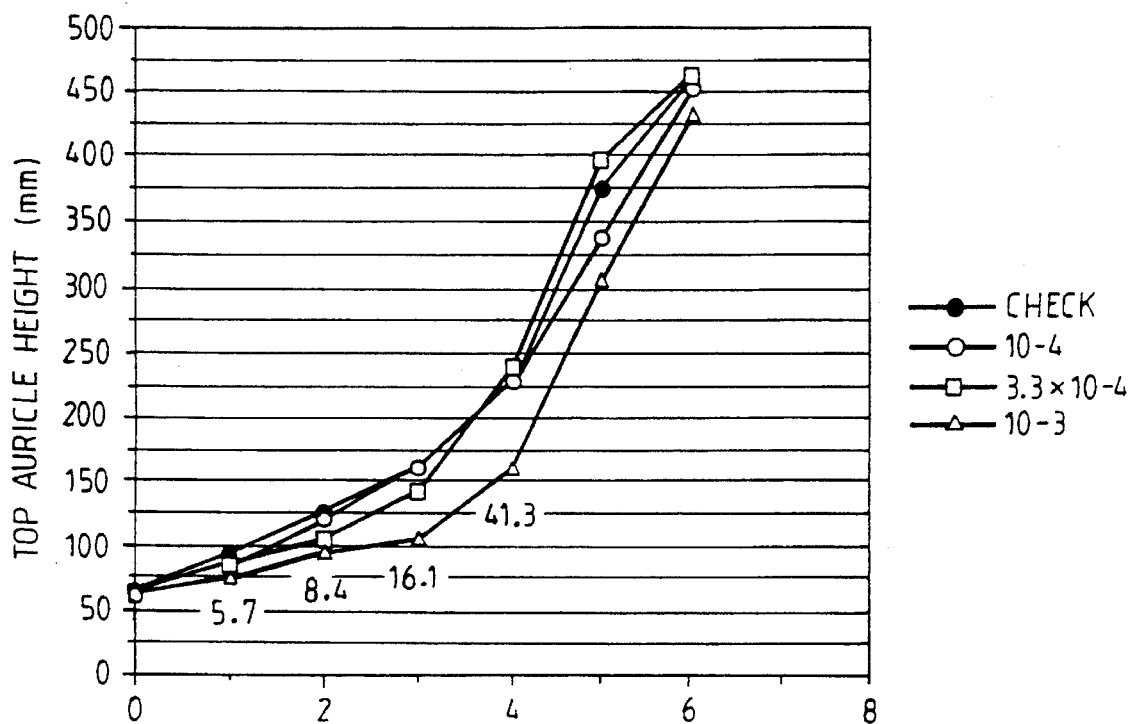
Fig. 23 SINGLE SPRAY OF EXO-DIHYDRO $A_5$ BARLEY HEARTLAND
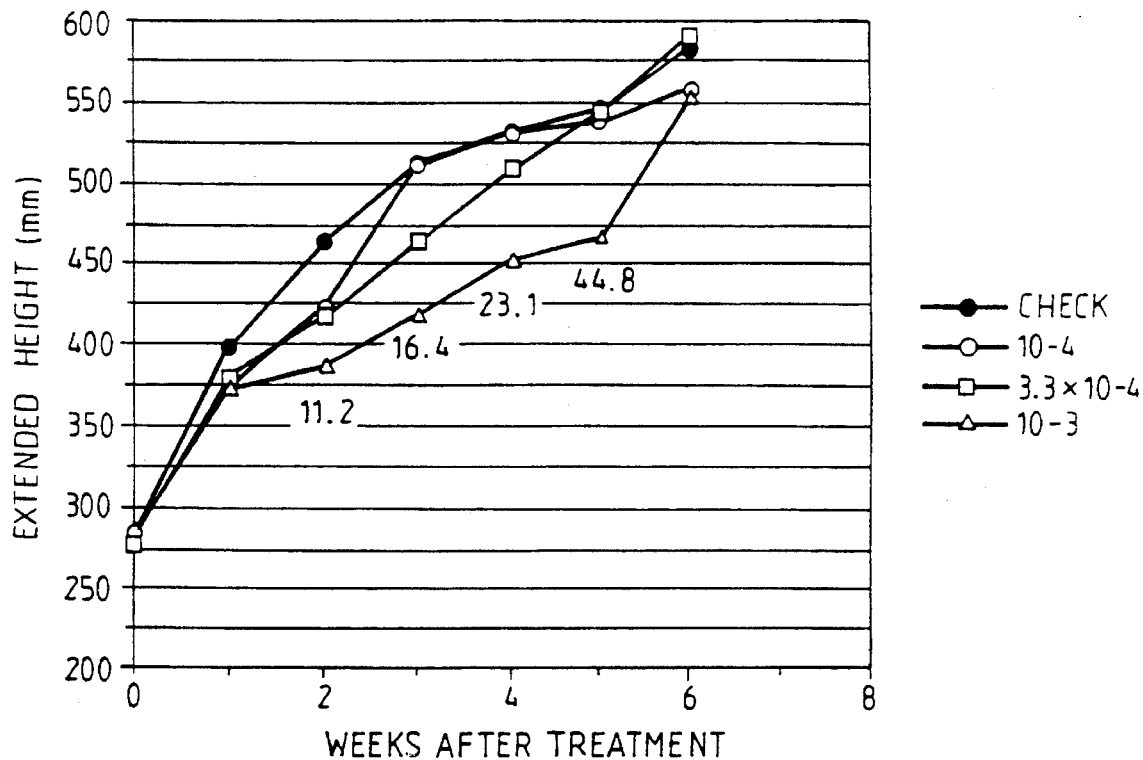
Fig. 24

Fig. 25 SINGLE SPRAY OF EXO-DIHYDRO $GA_5$ BARLEY, JACKSON
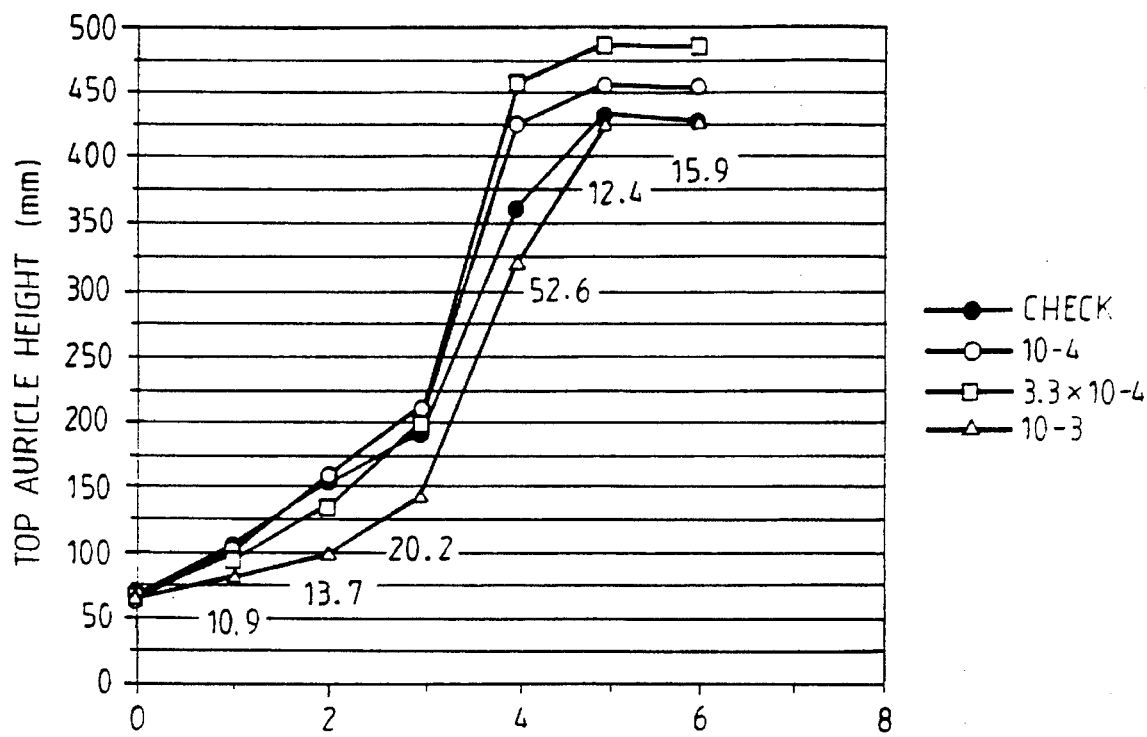
Fig. 26
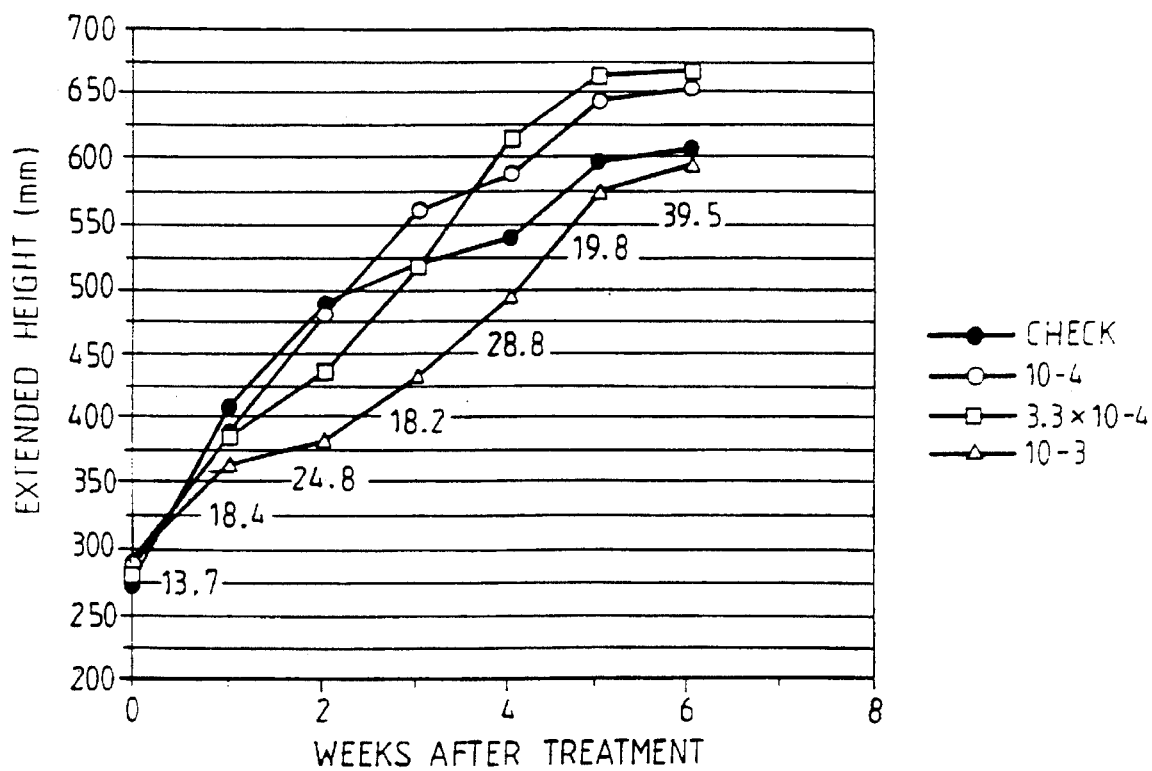

LEFT TO RIGHT
CONTROL WHEAT
CONTROL OATS
300 ppm C-16,17-DIHYDRO $GA_5$ WHEAT
300 ppm C-16,17-DIHYDRO $GA_5$ OATS
PHOTOGRAPH I

FOREGROUND - 300 ppm C-16,17 DIHYDRO $GA_5$
BACKGROUND - CONTROL
PHOTOGRAPH 2

LEFT - CONTROL OATS
RIGHT - 300 ppm C-16,17- DIHYDRO $GA_5$ OATS
PHOTOGRAPH 3

LEFT- 300ppm C-16,17-DIHYDRO GA₅
RIGHT- CONTROL
PHOTOGRAPH 4

LEFT - CONTROL WILD OATS
RIGHT - 300 ppm C-16,17-DIHYDRO GA$_5$ WILD OATS
PHOTOGRAPH 5
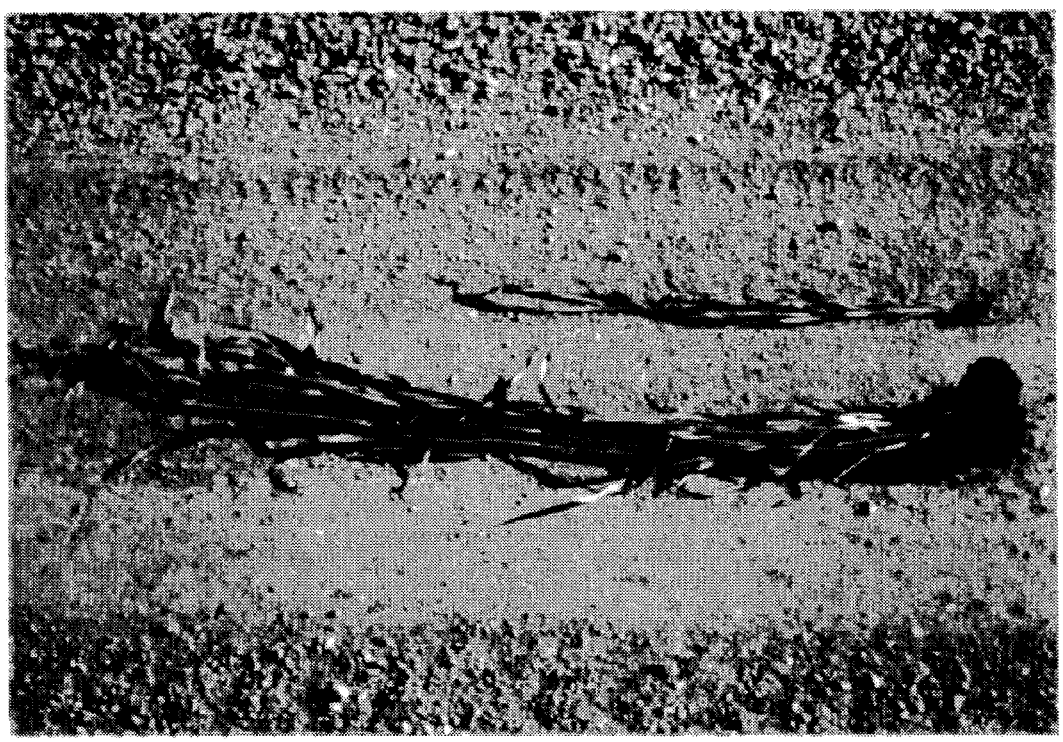

METHOD OF TREATING PLANTS OR PLANT TISSUES WITH C-16,17-DIHYDRO GIBBERELLINS

This application is a continuation (filed under 35 USC 371) of PCT application PCT/AU92/00426, filed Aug. 14, 1994.

This invention relates to a method of treating plants or plant tissues (including cuttings, roots, bulbs, corns, tubers, rhizomes and seeds) in order to induce a desired tissue morphology and/or a desired physiological state.

Numerous phytoactive substances are known which are used in agricultural and horticultural practice in order to promote desired physiological effects in higher plants. Such effects include promotion of flowering, weed control, inhibition of stem elongation (dwarfing), improvement of hardiness, promotion of rooting and inhibition of root or shoot growth in germinating seeds. Many available phytoactive substances have undesirable side effects and may give rise to toxic residues which tend to pollute the environment.

Naturally occuring gibberellins have found extensive use in agriculture and horticulture and can, for example, be used as components of compositions for promoting flowering. The so-called effector gibberellins (GAs), including $GA_1$ and $GA_3$, produce stem elongation in many plants and while this may in certain circumstances be desirable, often the converse is the case and it is preferable to retard stem elongation in order to produce dwarf plants. The control of flowering and stem elongation of higher plants is economically desirable for a number of reasons, including, but not restricted to enhancing earliness of flowering, ensuring uniformity of flowering, increasing the number of flowers produced, and reducing the height of the plant, thereby making it more resistant to falling over, or breakage, and also making it easier to train (i.e. orchard trees).

The literature makes it apparent that certain members of the gibberellin class of molecules will effectively promote flowering in many, but not all higher plants. However a major drawback to the use of those gibberellins which have been reported to promote flowering is the increased shoot and stem growth (elongation) caused by application of such gibberellins. Further, these overt side effects may make the plant more susceptible to being damaged, or falling over (being lodged) as a result of rain, hail or snow or simply as a result of sheer overgrowth. Additionally, it is known that application of many gibberellins to woody angiosperm species is known to be deleterious to next year's flowering. That is to say application of a gibberellin in order to enhance fruit set or fruit quality may inhibit the following year's flower crop.

Reducing the shoot growth in a flowering plant is extremely useful in many circumstances. First it makes the plant more resistant to adverse weather conditions in the field, such as wind, rain, hail and snow. Secondly, it makes the plant more compact, more stocky, and more resistant to falling over (technically known as "lodging") as a result of the aforementioned weather conditions and/or as a result of heavy fruit or seed or grain production. Thirdly, in orchard situations a more compact nature of the shrub or tree is extremely valuable for a variety of reasons, including ease of tending the tree, picking the fruit, applying other treatments and reducing the necessity to prune the tree or shrub. Also, shoot growth resulting either from the presence of high levels of endogenous gibberellins, or induced by gibberellins applied to the plant, can compete with growth and development of fruit, seed or grain, thereby reducing the final yield.

A high concentration of endogenous effector gibberellins can be undesirable in plants which have been subjected to conditions likely to cause physiological damage. Thus the presence of effector gibberellins such as gibberellins $GA_1$ and/or $GA_3$ in recently transplanted trees and woody shrubs can give rise to reduced hardiness resulting in diminished survival.

We have now developed a procedure for promoting a desired tissue morphology and/or physiological state in a higher plant, which comprises applying to the plant an amount of a C-16,17-dihydro gibberellin or C-16,17-dihydro gibberellin precursor.

The use of C-16,17-dihydro gibberellins for this purpose has not hitherto been suggested. In fact in their review of the activities of number of gibberellins, including seven C-16,17-dihydro gibberellins, Brian et al (Phytochemistry (1967), 6, pp. 1475–1499) concluded that "None of the compounds listed in the tables proved inhibitory in our tests, Many were inactive in all four tests". Furthermore Brian et al contains no indication that C-16,17-dihydro gibberellins might possess useful growth inhibiting or florigenic properties.

As will be described in more detail below, the desired tissue morphology and/or physiological states can be promoted according to the invention without the often undesired effects (including shoot or stem elongation) associated with the application of so-called "effector" gibberellins.

Although the precise mechanism of action of C-16,17-dihydro gibberellins when applied in accordance with the invention is not known, it is believed that they produce an at least partial inhibition of formation of effector gibberellins in the plant. It is theorized that this is a result of an at least partial inhibition of gibberellin 3β-hydroxylase activity in the plant. Gibberellin 3β-hydroxylase is a naturally occurring enzyme which mediates the interconversion of certain gibberellins in plant by hydroxylating them at position C-3. Thus many plants obtain their endogenous effector gibberellins by conversion from precursors in the biosynthetic pathway.

For example many plants convert gibberellin $GA_{20}$ to gibberellin $GA_1$ and/or gibberellin $GA_{20}$ to gibberellin $GA_5$ and then to gibberellin $GA_3$.

Use of a C-16,17-dihydro gibberellin or C-16,17-dihydro gibberellin precursor in accordance with the invention is believed to inhibit formation of endogenously produced effector gibberellin $GA_1$ and/or $GA_3$, and will also inhibit their formation from certain exogenously applied gibberellins. The invention is thus particularly applicable to the treatment of plants which obtain their endogenous effector gibberellins by conversion from precursors by hydroxylating them at position C-3 by a pathway which involves a gibberellin 3β-hydroxylase.

It may also be applicable to situations where the desired morphology can be obtained by blocking 2β hydroxylation of active gibberellins and their production.

Thus according to one aspect of the present invention, there is provided a method for promoting a desired tissue morphology and/or physiological state in a higher plant, which comprises applying to the plant an amount of a C-16,17-dihydro gibberellin or C-16,17-dihydro gibberellin precursor effective to produce an at least partial inhibition of formation of effector gibberellins (e.g. gibberellins $A_1$ and/or $A_3$ among others).

While inhibition of formation of effector gibberellins is presently believed to contribute to the beneficial effects obtainable by applying a C-16,17-dihydro gibberellin or C-16,17-dihydro gibberellin precursor in accordance with the invention, the invention is not intended to be limited to any particular theoretical explanation of the observed results. Thus the invention according to preferred aspects thereof may be defined in terms of the macroscopic effects obtained, such as, for example, enhanced induction of flowering, improving fruit quaility, inhibiting ripening of fruit, improving fruit set, controlling growth of weeds and other effects.

Thus according to a further aspect of the invention, there is provided a method for promoting flowering in a higher plant, which comprises applying to the plant an amount of a C-16,17-dihydro gibberellin or C-16,17-dihydro gibberellin precursor effective to induce flowering.

The finding that C-16,17-dihydro gibberellins or C-16,17-dihydro gibberellin precursors can promote flowering without inducing significant stem elongation, and indeed can promote flowering while often retarding stem elongation, is considered to be particularly surprising, because the extensive literature on the known physiological effects of available gibberellins shows numerous instances where shoot growth is enhanced with or without promotion of flowering, but never where promotion of flowering is achieved together with a reduction, inhibition or retardation of shoot growth.

The invention further provides:

a method for improving fruit quality in a higher plant, which comprises applying to the plant an effective amount of a C-16,17-dihydro gibberellin or C-16,17-dihydro gibberellin precursor.

a method for inhibiting ripening of fruit of a higher plant plant, which comprises applying to the plant an effective amount of a C-16,17-dihydro gibberellin or C-16,17-dihydro gibberellin precursor.

a method for improving fruit set in a higher plant, which comprises applying to the plant an effective amount of a C-16,17-dihydro gibberellin or C-16,17-dihydro gibberellin precursor.

a method of controlling growth of weeds in an area of land which comprises applying to said land area a C-16,17-dihydro gibberellin or C-16,17-dihydro gibberellin precursor.

a method for retarding bud break in a higher plant, which comprises applying to the plant an effective amount of a C-16,17-dihydro gibberellin or C-16,17-dihydro gibberellin precursor.

a method for retarding shoot growth (with or without promoting flowering) in a higher plant, which comprises applying to the plant an effective amount of a C-16,17-dihydro gibberellin or C-16,17-dihydro gibberellin precursor.

a method for promoting tillering and/or bud release in a higher plant, which comprises applying to the plant an effective amount of a C-16,17-dihydro gibberellin or C-16,17-dihydro gibberellin precursor.

a method for inducing male sterility in a higher plant, which comprises applying to the plant an effective amount of a C-16,17-dihydro gibberellin or C-16,17-dihydro gibberellin precursor.

The C-16,17-dihydro gibberellins and C-16,17-dihydro gibberellin precursors useful in carrying out methods of the invention may be characterised by the following general formulae Ia, Ib, Ic, Id and Ie:

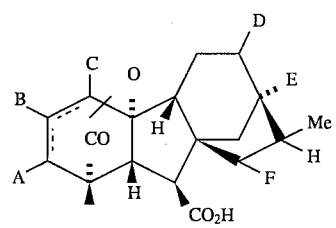

Ia

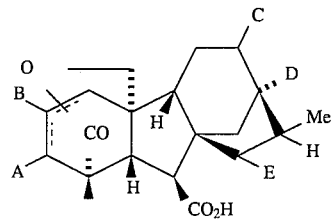

Ib

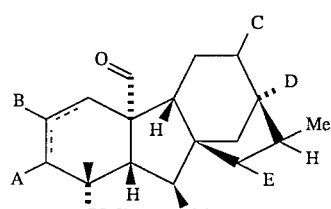

Ic

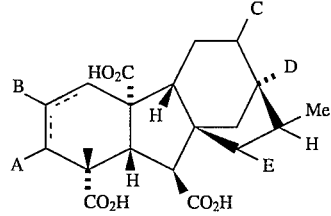

Id

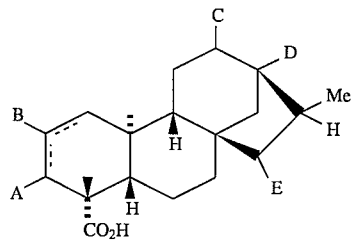

Ie wherein A,B,C,D, E and F independently represent hydrogen atoms or hydroxyl groups and the dotted line represents one optional double bond either between the carbon atoms in positions 1 and 2 or between the carbon atoms in positions 2 and 3.

16,17-dihydro $GA_5$ is a particularly preferred compound for use in accordance with the invention, particularly for use as a growth inhibitor. Also 16,17-dihydro $GA_3$ is a particularly preferred compound for use in accordance with the invention, particularly where a flowering-promoting effect is desired. Specifically 16,17-dihydro $GA_3$ has a flowering-promoting effect similar to that obtainable with $GA_3$, but essentially without the growth promotion effects associated with the latter compound.

In certain applications using componds of formula Ia, one optional proviso is that where B, C and D represent hydrogen and A represents hydroxy, a double bond is present between the carbon atoms in positions 1 and 2. Another optional proviso is that where A, B, C and D represent hydrogen and E represents hydroxy, a double bond is present between the carbon atoms in positions 1 and 2 or 2 and 3.

16,17-dihydro gibberellins for use in accordance with the invention may be produce by hydrogenating the corresponding 16,17-dehydro gibberellin, e.g. with $Pd/H_2$.

In the above formulae (wherein Formula Ie repesents a typical 16,17-dihydro gibberellin precursor based on kaurenoic acid) the ent-gibberellane skeleton may be numbered as follows

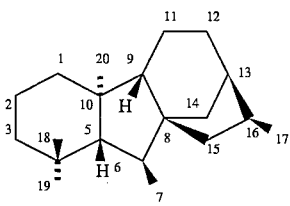

Examples of compounds which may be used in accordance with the invention include C-1,2-didehydro, C-16,17-dihydro gibberellins, for example C-16,17-dihydro $GA_3$. Other examples include C-16,17-dihydro $GA_{20}$; C-16,17-dihydro, 2,3 dehydro $GA_9$; C-16,17-dihydro $GA_{12}$; C-16,17-dihydro $GA_{15}$ and C-16,17-dihydro $GA_{53}$.

Further examples include the C-2,3 didehydro derivatives of C-16,17-dihydro $GA_3$; of C-16,17-dihydro $GA_{20}$ (this compound being C-16,17-dihydro $GA_5$), of C-16,17-dihydro $GA_{12}$, of C-16,17-dihydro $GA_{15}$ and of C-16,17-dihydro $GA_{53}$.

Most preferably, the C-16,17-dihydro gibberellin used in accordance with the invention is C-16,17-dihydro $GA_5$ of Formula IIa or IIb.

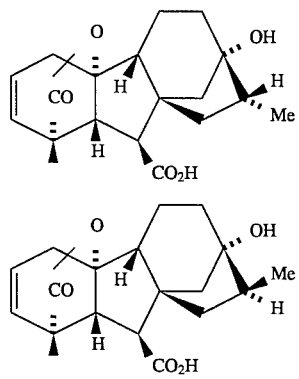

In the above formulae, the 16-exo compound has the 16-R configuration and the 16-endo compound has the 16-S configuration.

The 16,17-dihydro gibberellins used in accordance with the invention include compounds having one or more of the following structural features:

A. 2,3 unsaturation (i.e. as in 16,17-dihydro $GA_5$)
B. 1,2 unsaturation (i.e. as in C-1,2-dehydro 16,17-dihydro $GA_9$)
C. substitution with one or two hydroxy groups at one or more of C-1, C-11, C-12, C-13 and C-15
D. substitution with three hydroxy groups at one or more of C-1, C-11, C-12, C-13 and C-15
E. substitution with four hydroxy groups at one or more of C-1, C-11, C-12, C-13 and C-15.

Examples include 16,17-dihydro $GA_5$;

16,17-dihydro C-2,3-dehydro $GA_9$;

2,3-dehydro, C-12-hydroxy, 16,17-dihydro $GA_5$ and 2,3-dehydro, C12,15-dihydroxy 16,17-dihydro $GA_5$.

As indicated above, application of a C-16,17-dihydro gibberellin in accordance with the invention can be effective to promote flowering without producing simultaneous stem elongation. In fact promotion of flowering with simultaneous reduction, inhibition or retardation of shoot growth has been observed.

Thus according to a further aspect of the invention there is provided a method of promoting flowering in a higher plant which comprises applying to the plant an amount of a C-16,17-dihydro gibberellin effective to induce flower formation.

Preferably the C-16,17-dihydro gibberellins are as defined above.

The C-16,17-dihydro gibberellins used in accordance with the invention may be applied in the form of free acids or as salts or esters thereof. Suitable salts and esters include the sodium and potassium salts and the $C_{1-4}$ carboxylic acid esters.

The gibberellins may be used in accordance with the invention alone or with other plant growth regulators, for example chemical thinning agents.

Further the method of the invention may be carried out in the open, i.e. in the field, or in a glasshouse environment.

Particularly in connection with that aspect of the invention concerned with promotion of flowering, the C-16,17-dihydro gibberellins may be applied under photoperiod and temperature conditions which are inductive, marginally inductive, or non-inductive of flowering. Flowering may be promoted under any of these conditions while at the same time reducing unneeded or unwanted shoot growth.

The application of C-16,17-dihydro gibberellins in accordance with the invention may desirably be carried out in autumn, so as to improve cold hardiness or retard the next season's bud break, or in early spring, or late spring or early summer, either prior to normal flower initiation or during early stages of flower differentiation, or during early stages of floral development. Good results have been obtained at all of these stages. Although multiple applications of the C-16,17-dihydro gibberellin may be made, significantly improved flowering, with concomitant shoot length reduction, can often be achieved with a single application.

The method of application of the C-16,17-dihydro gibberellin is not thought to be particularly critical and may be accomplished, for example, by spraying a solution or suspension of the C-16,17-dihydro gibberellin to whole plants, or by application to seeds or roots or bulbs, corms or rhizomes, together with a suitable carrier. The addition of conventional adjuvants such as wetting agents and dispersants may prove to be beneficial in some agronomic situations.

Only small quantities of C-16,17-dihydro gibberellin need be applied in accordance with the invention. The precise dose will depend upon the desired tissue morphology or physiological state which is desired to be induced and the plant species. Thus experiments have shown that in certain species, e.g. lettuce, root length is inhibited at concentrations of 16,17-dihydro GA5 in the range of $10^{-10}$ to $10^{-7}$M, but is promoted at concentrations of $10^{-6}$M and higher.

For a given species, the required dosage and treatment regime can readily be determined by carrying out appropriate experiments, e.g. along the lines of those described herein.

As a general guide dosage rates of from 0.1 to 1000 micrograms of dihydro GA per gram of actively growing plant tissue, especially from 2 to 100 micrograms of dihydro GA per gram of actively growing plant tissue have been found to give useful results, and for stimulating flowering, satisfactory results have been obtained with as little as 2 micrograms per plant.

The amount of dihyro gibberellin or dihydrogibberellin precursor applied in accordance with the invention may also be expressed in terms of a proportion of the weight of fresh or dry plant tissue. Expressed in this way the applied amount is preferably up to 1000 micrograms/gram fresh weight, especially from 1 to 1000 micrograms/gram fresh weight. Most preferably, the amounts applied are from 2 to 1000 micrograms/gram fresh weight, especialy from 2 to 500 micrograms/gram fresh weight. Optimally, the applied amounts are from 2 to 333 micrograms/gram fresh weight, especially from 2 to 100 micrograms/gram fresh weight. (For most plant species, the ratio of fresh:dry weights is 10:1–6:1).

Dihydro gibberellins may be formulated for use in accordance with this invention at concentrations up to 5000 ppm ($1.5 \times 10^{12}$M). Most preferably the minimum concentration is preferably 0.1 ppm (when applied as a seed soak or soil drench, lower concentrations may be used as detailed below). A preferred concentration range is 1∝1000 ppm.

Concentrations of from 200 ppm, preferably from 5–350 ppm of the C-16,17-dihydro gibberellin will give satisfactory results, especially when applied as a foliar spray. With certain species (for example oilseed rape), application rates of from 10 to 100 times higher than those mentioned above may be required. Lower concentrations have been found to be effective when used as a seed soak or soil drench, for example concentrations in the range of $10^{-12}$ to $10^{-7}$ molar, although preferably the minimum concentration is at least $10^{-10}$M.

Although the method of the invention can be carried out using a C-16,17-dihydro gibberellin as the sole plant growth modifying agent, other plant growth regulators such as cytokinins or even shoot elongation-promotive gibberellins such as gibberellin $A_1$ or gibberellins $A_3$ may be additionally used. Thus, for example, gibberellins $A_1$ or gibberellin $A_3$ or other gibberellins such as the 3β-hydroxylated gibberellins $A_4$ and $A_7$ may be usefully included in the treatment in order to counteract an excessively intense shoot growth reduction caused by application of the C-16,17-dihydro gibberellin.

The application of C-16,17-dihydro gibberellins in accordance wih the invention can be used to produce advantageous effects which can manifest themselves in many different ways. Particularly, it has been found to be possible to obtain many of the desirable physiological effects hitherto produced by applying other gibberellins, but without producing excessive shoot growth, excessive overgrowth of the stem and diminished flowering the next year in woody angiosperms.

BRIEF DESCRIPTION OF DRAWINGS

FIGS. 5, 6, 7, 7a, 8, 9, and 10 show the effect of GA dose on second leaf sheath length.

FIGS. 19–26 shows the effect of different dosages of $GA_5$ on barley height.

Figure 1:
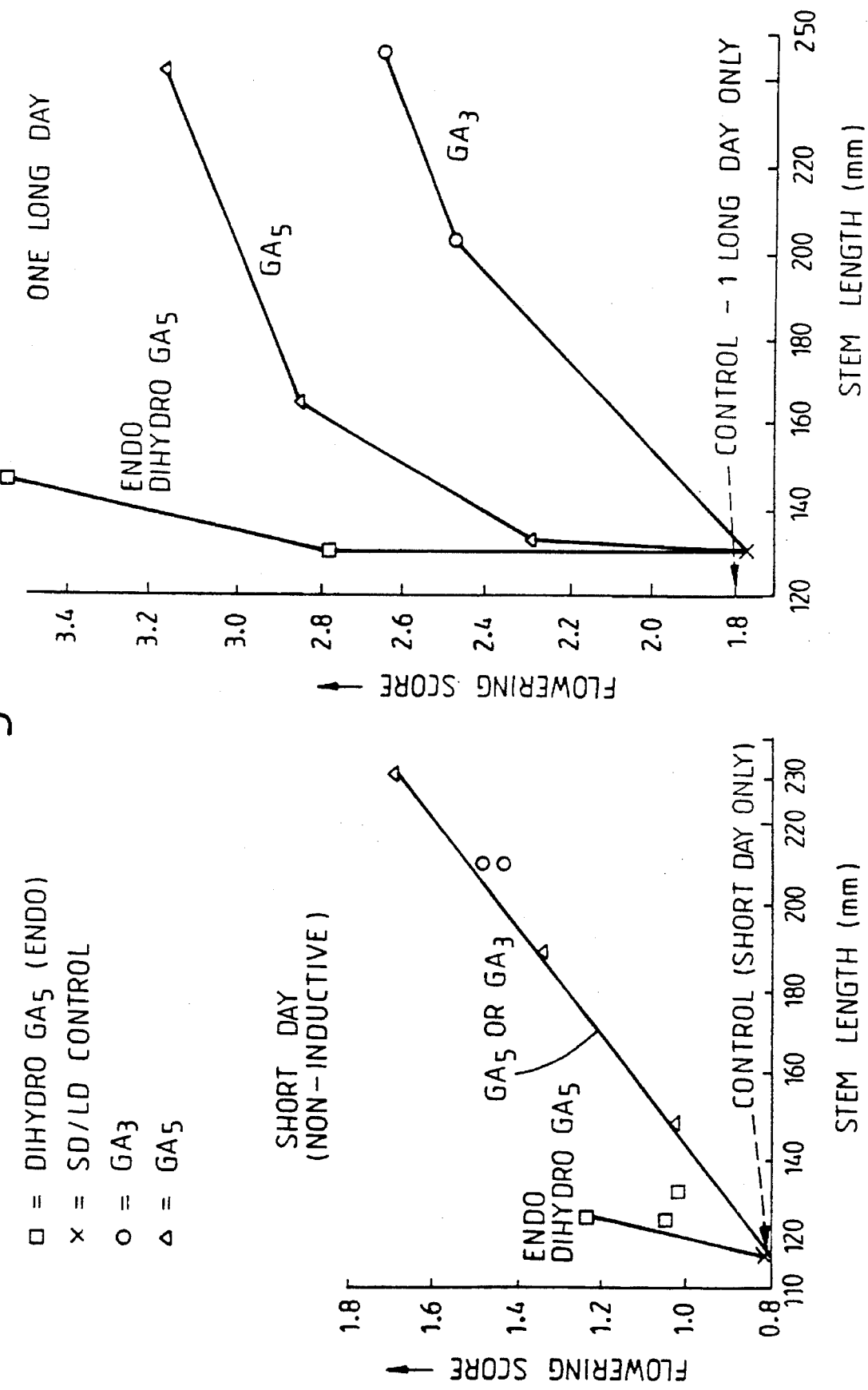
FIG. 1 show that endo-dihydro GA5 alone is effective in promoting flowering, without producing the stem extension observed following application of GA3 or GA5.

Photographs 1–5 present comparisons of controls with plants treated with C-16,17-dihydro $GA_5$.

Specific examples of effects obtainable in accordance with the invention include the following:

(1) thinning of wine and table grapes without inhibition of the following year's flowering (2) increased flowering in wine grapes (3) improvement of the fruit quality in cherries, while reducing shoot growth.

(4) production of parthenocarpic fruit without inhibition of the following year's flowering and without increased shoot growth which results from known treatments with $GA_3$. To achieve this it is desirable to include an additional gibberellin such as $GA_4$.

(5) promotion of flowering in woody angiosperms so as to prevent bienniality without causing increased vegetative shoot elongation, or with concomitant reduction of shoot growth.

(6) maintaining green fruit and inhibiting ripening (on the tree) in citrus and other fruits. This effect is achievable without the negative side effects (for example increased shoot growth and reduced next year's flowering) resulting from known treatments involving the use of $GA_3$.

(7) increasing fruit set without inhibition of next year's flowering (as is caused by known treatments using $GA_3$ or $GA_{4/7}$) with a reduction of vegetative shoot growth, thereby improving the allocation of photosynthate to the developing fruit.

(8) as a fruit thinning agent (at relatively high doses) without inhibiting next year's flowering and with a reduction in shoot growth of adjacent shoots, therefore improving the allocation of photosynthate to developing fruit.

(9) increasing fruit yield brought about by favouring and enhancing the redistribution of photosynthate to the fruit or grain head (this effect would primarily result from the reduction of vegetative growth) and is useful for a range of crops including strawberries, cereal, legumes, and fruit trees such as apples and pears.

(10) induction of male sterility particularly in the production of hybrid corn, wheat and sorghum seed.

(11) restoration of male fertility in varieties having diminished male fertility or male sterile lines.

(12) weed control. Promotion of flowering of longday weeds, either prematurely (e.g. in early spring or autumn or early winter) or in mid-season. This would cause longday weeds to flower, but not bolt and the weeds would then be shaded by the crop plants normal growth.

(13) weed control e.g. by promoting germination of weed seeds, but retarding their subsequent growth, or by breaking bud dormancy, but allowing for only a very reduced weed growth. Application of C-16,17-dihydro gibberellins in accordance with the invention inhibits the early growth of weed seedlings such as wild oats by yielding a young seedling with a very reduced shoot growth (see Photographs 1–5) and in fact even yielding a toxic effect which would be unable to compete with the main crop (the main crop already being established). Alternatively, the main crop would be sown deeply enough so as to avoid the influence of the applied C-16,17-dihydro gibberellin. The resulting weed seedlings with slowed root growth would also be more prone to drought.

(14) weed control by prevention of flowering of shortday annual weeds under marginally inductive long nights, without the negative side effects that would be expected from the use of gibberellin $A_3$ on an accompanying longday or day neutral crop plant.

(15) priming or stimulation of uniform and more complete germination (by seed soak) without the overt elongation of the germinating seedling that is observed to occur with a gibberellin such as $GA_3$ or $GA_{4/7}$ mixture

(16) promotion of rooting in hard-to-root varieties e.g. where high endogenous gibberellin levels prevent rooting. Application of C-16,17-dihydro gibberellins in accordance with the invention may be accompanied by the application of an auxin such as indolebutyric acid or NAA.

(17) the treating of peonies, via the rhizome, to get more floral branches, but without the excessive elongation which is known to be induced by use of $GA_3$ (see M. R. Evans, W. O. Anderson, H. F. Wilkins [1990] Temperature and $GA_3$ Effects on emergence and flowering of potted *Paeonia laetifolia*. Hort. Science 25:923–924).

(18) the treating of cauliflower to alter the timing of flower (curd) development (e.g. advance curd development), but without causing untoward elongation of the base of the curd, as may occur with use of $GA_3$ or $GA_{4/7}$ (see R. Booij and reference cited therein [Effects of gibberellic acids on time of maturity and on yield and quality of cauliflower. Ntherlands J. of Agric. Science 38:641–651 (1990)].

(19) in the malting of barley grain significant amounts of stored assimilate are diverted into the developing root and shoot of the germinating grain. This is wasteful and is considered a loss by the brewing and malting industries. It is presently controlled in some countries by the use of bromate ion, the safety of which can now be questioned, followed by application of $GA_3$, the latter stimulating α-amylase production over and above that obtained by use of the malted grain alone, with or without bromate ion. Influencing (retarding) the allometric distribution of stored assimilate from the starchy endosperm of the grain into the root and shoot can be accomplished by imbibing the seed in the presence of low levels (ca. $10^{-5}$ to $10^{-10}$M) of C-16,17-dihydro gibberellins. This may then be followed by treatment with $GA_3$ to induce α-amylase production (the α-amylase breaks down starch to sugar).

(20) prevention of precocious germination (sprouting) on the seed head for grain crops by antagonizing the production of bioactive effector gibberellins.

(21) increasing cold hardiness by application of dihydro gibberellins. The production of excessive shoot growth in late summer and fall which would be tender and frost susceptible, is reduced, by antagonizing production of bioactive endogenous effector gibberellins.

(22) increasing drought-hardiness by providing a more compact plant shoot by antagonizing production of bioactive gibberellins. Root growth would be proportionately less affected due to differential retention in the shoot. Plants will then have more efficient water use and be able to better withstand transplanting.

(23) "safening" of a plant for subsequent sprays with herbicides. In this case, the main crop plant would be sprayed with the C-16,17-dihydro gibberellin several days to weeks before the proposed herbicide treatment. The dihydro gibberellin would retard growth of the crop plant, thereby rendering it more resistant to the herbicide.

(24) retarding growth of both vegetative and floral parts of amenity grasses, and even inhibiting flowering of short-day induced amenity grasses, thereby providing a more useful grass for lawns, parkways and golf courses.

(25) retarding bud break of both floral and vegetative buds thereby allowing for a delayed and more uniform bud break after, for example, the damage of frost has passed, or in the case of potted plants, to allow for staggered, or delayed bud break, with uniformity of bud break being brought about, where necessary, by subsequent use of an effector gibberelin such as GA1, GA3, GA4 or GA7.

(26) promoting of tillering, especially in grain crop, and in amenity grasses, i.e. turf grasses

(27) total prevention of flowering

(28) increased prostrate growth form

(29) promotion of male flowers (cone buds) in pinaceae.

(30) reduction in seed set/production in Graminal species.

Species which may be treated in accordance with the invention include wheat, barley, oats, maize, sorghum, amenity grasses, native grasses and other members of the Gramineae, Spathyphyllum, Zantedeschia and other members of the Araceae, dicotyledenous crop plants such as cotton, sunflower, oilseed rape, soybean, field pea, native flowering plants, woody angiosperm trees and shrubs (including azealea, grape and shade trees and orchard trees), and gymnosperm amenity trees and seed orchard trees.

The invention will now be described in more detail with particular reference to the following examples.

EXAMPLE 1

Promotion of Flowering in *Lolium temulentumn*

Plants of the species *Lolium temulentum* were grown under both non-inductive short day (SD) and one marginally inductive long day (LD) conditions.

Plants in each set were treated on 4th Jul. 1990 with one of the following treatments and control plants received no gibberellin

| Set | Treatment |
|-----|-----------|
| SD  | None (control) |
| LD  | " |
| SD  | endo-dihydro GA5 |
| LD  | " |
| SD  | GA3 |
| LD  | " |
| SD  | GA5 |
| LD  | " |

Each treatment consisted of applying the stated gibberellins as a microdrop to the leaf at a rate of 1 to 25 micrograms per plant.

The results are set out in graphical form in the atached FIG. 1 from which it can be seen that endo-dihydro GA5 alone is effective in promoting flowering, without producing the stem extension observed following application of GA3 or GA5.

EXAMPLE 2

Promotion of Flowering in Xanthium

Plants of the species genus Xanthium were grown under marginally inductive short day (SD) conditions.

Plants were treated with one of the following three treatments and control plants received no gibberellin

| Set | Treatment |
| --- | --- |
| A | None (control) |
| B | endo-16,17-dihydro GA5 |
| C | GA5 |
| D | endo-16,17-dihydro, 15β-OH GA5 |
| E | endo-16,17-dihydro GA5 + 10 μg GA3 |

Each treatment consisted of applying the stated gibberellins as a microdrop in ethanol at a rate of 5 to 50 micrograms per plant, within which range an optimal dose of the stated dihydrogibbberlin could be found. However a very high dose inhibited flowering.

Figure 2:
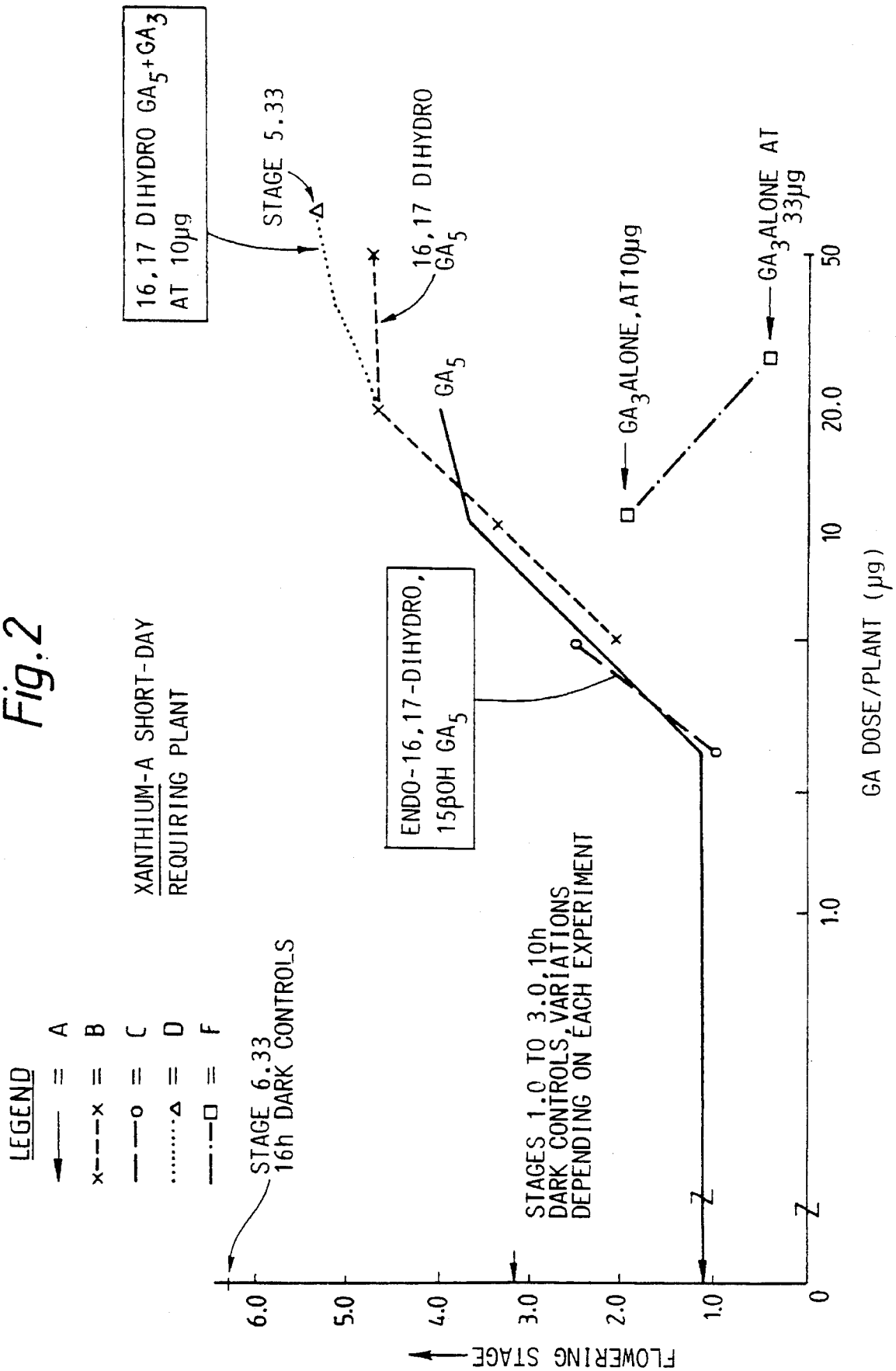
FIG. 2 shows that 16,17-dihydro GA5 can be used to promote flowering under marginally inductive short day conditions.

The results on Xanthium are set out in graphical form in the atached FIG. 2 and shows that 16,17-dihydro GA5 can be used to promote flowering under marginally inductive short day (long night) conditions. In the experiments using GA3 and 16,17-dihydro GA5 in combination, the flowering-promoting effect of 16,17 dihydro GA5 was enhanced by addition of an optimal amount of $GA_3$.

Similar results in plants of the genus Pharbitis, also grown under marginally inductive SD conditions were obtained, with D above, and also 16,17-dihydro $GA_3$ being especially effective.

EXAMPLE 3

Germination of Barley Seeds

Barley seeds were germinated on endo-C16,17-dihydro GA5 solutions and harvested after either 72 or 96 hours. 72 h results are expressed as shoot or root weight per 50 seeds. 96 h results are expressed as shoot or root weight per 10 seeds.

Figure 3:
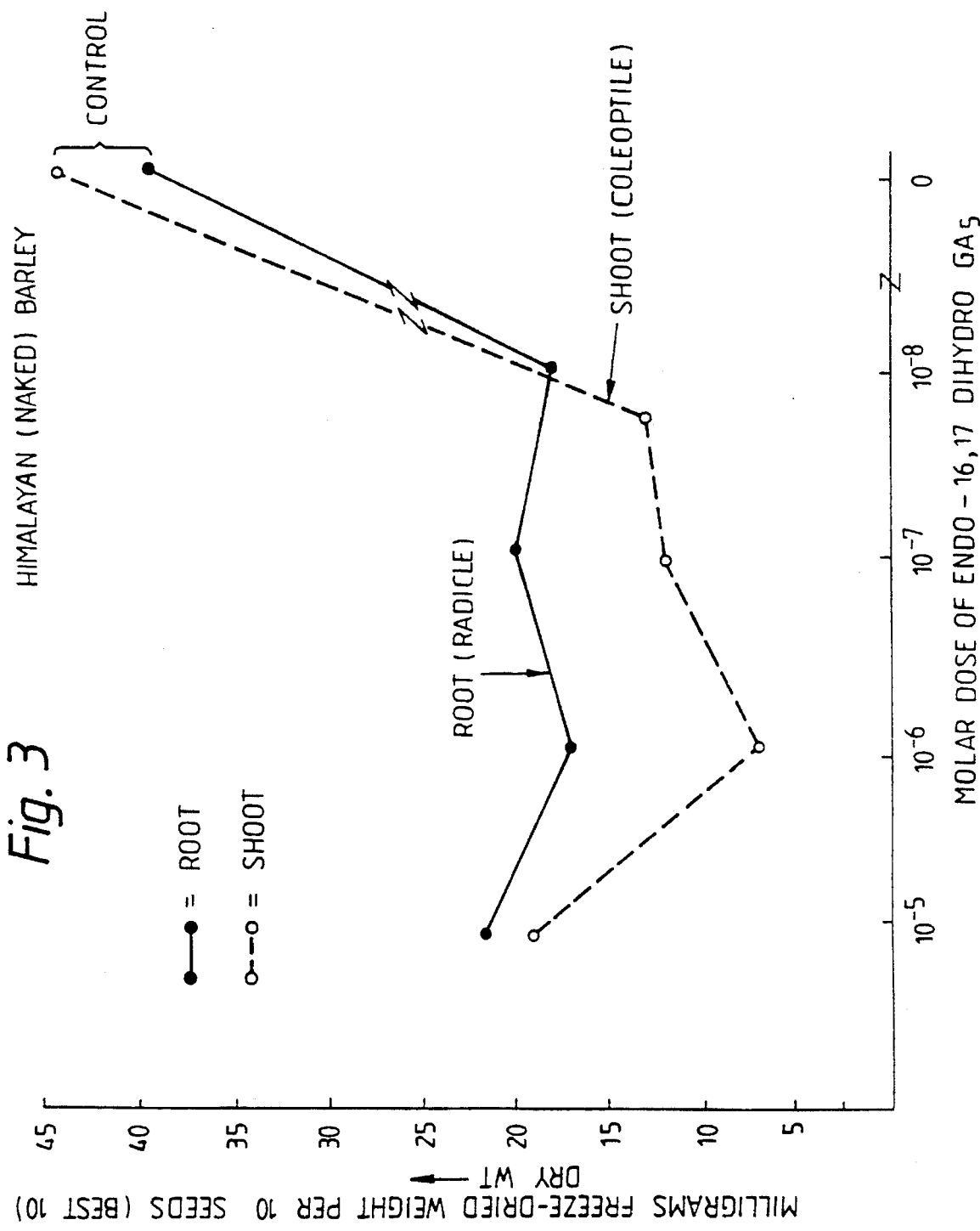
FIGS. 3 and 4 show that diversion of stored carbohydrate into root and shoot is significantly diminished.
Figure 4:
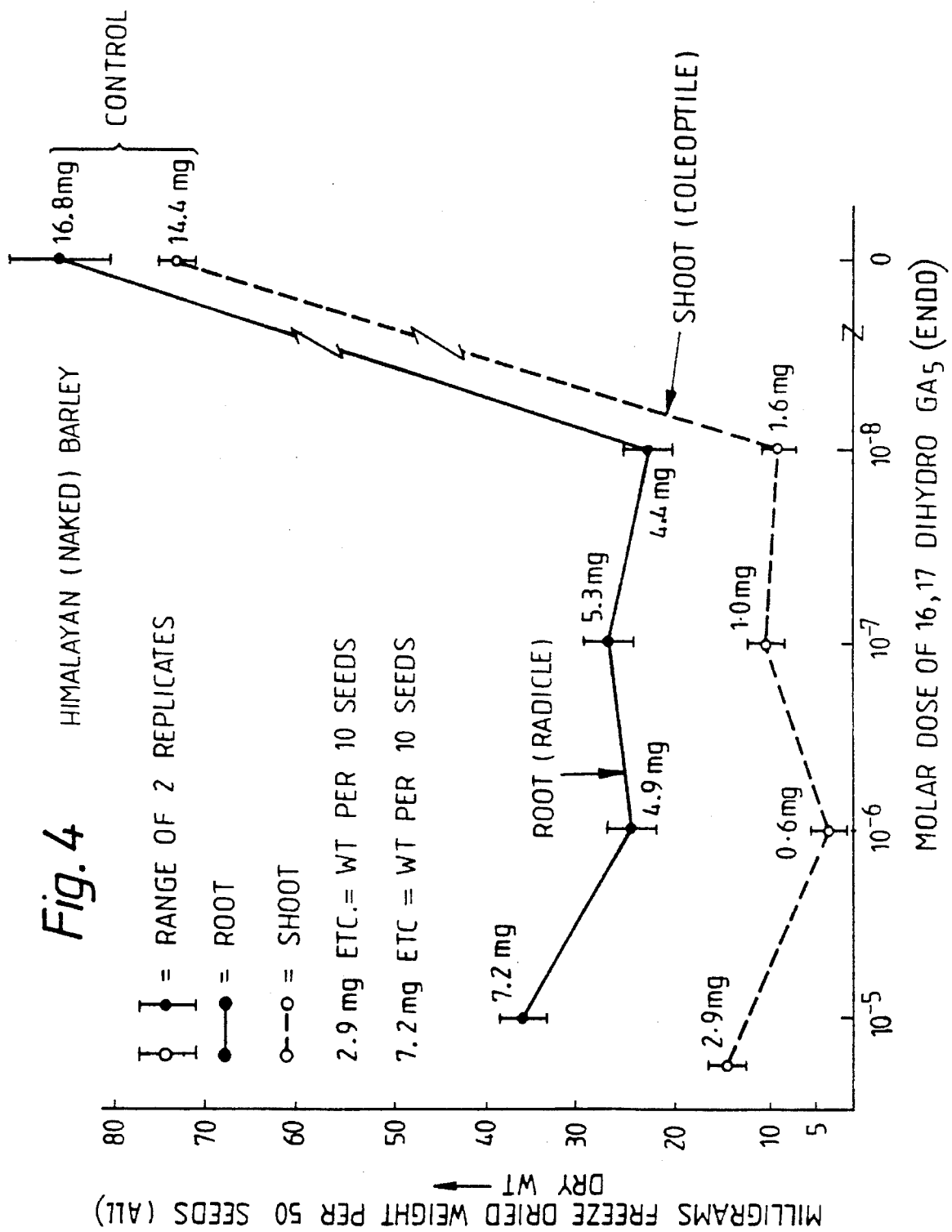
Figure 5:
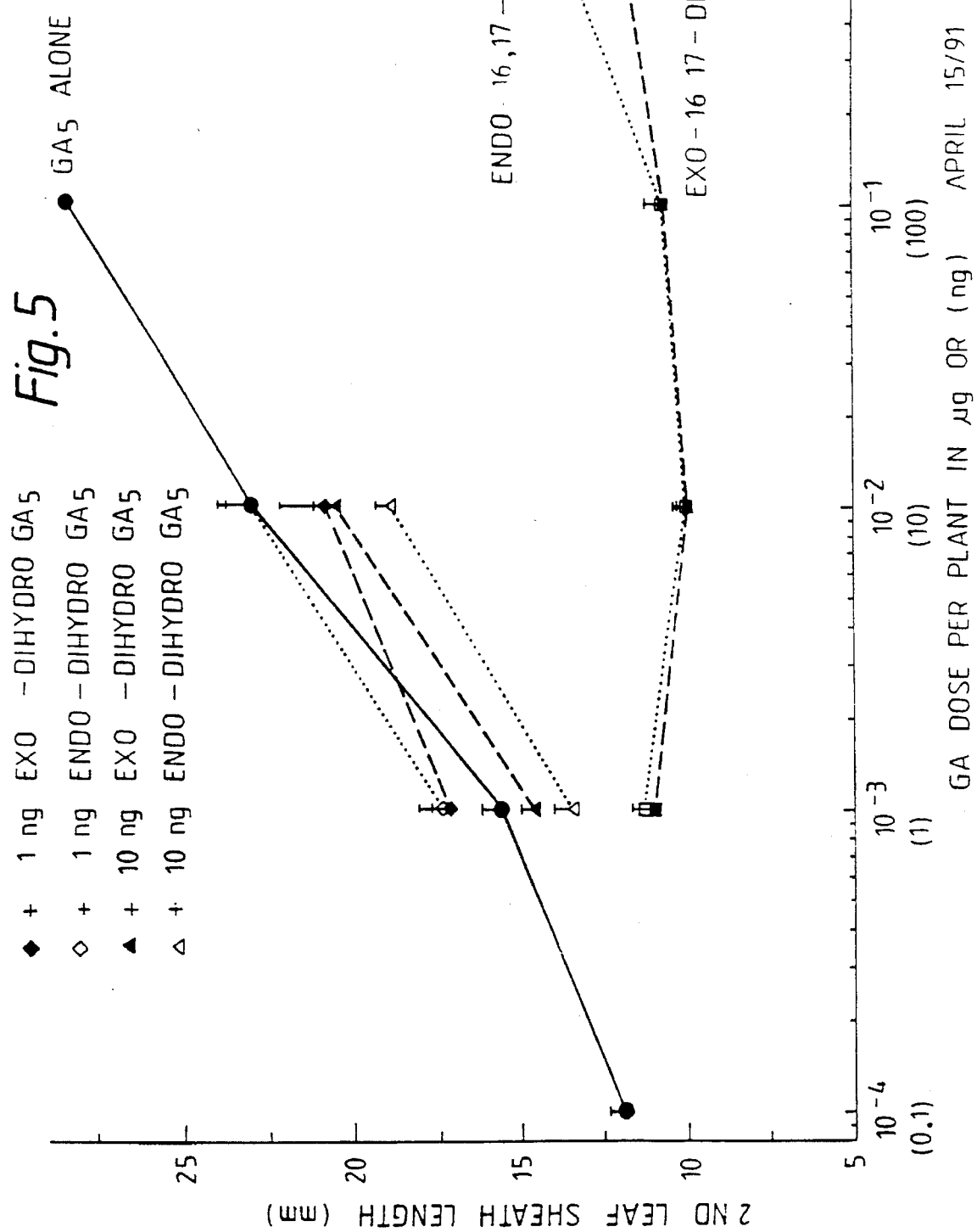
Figure 6:
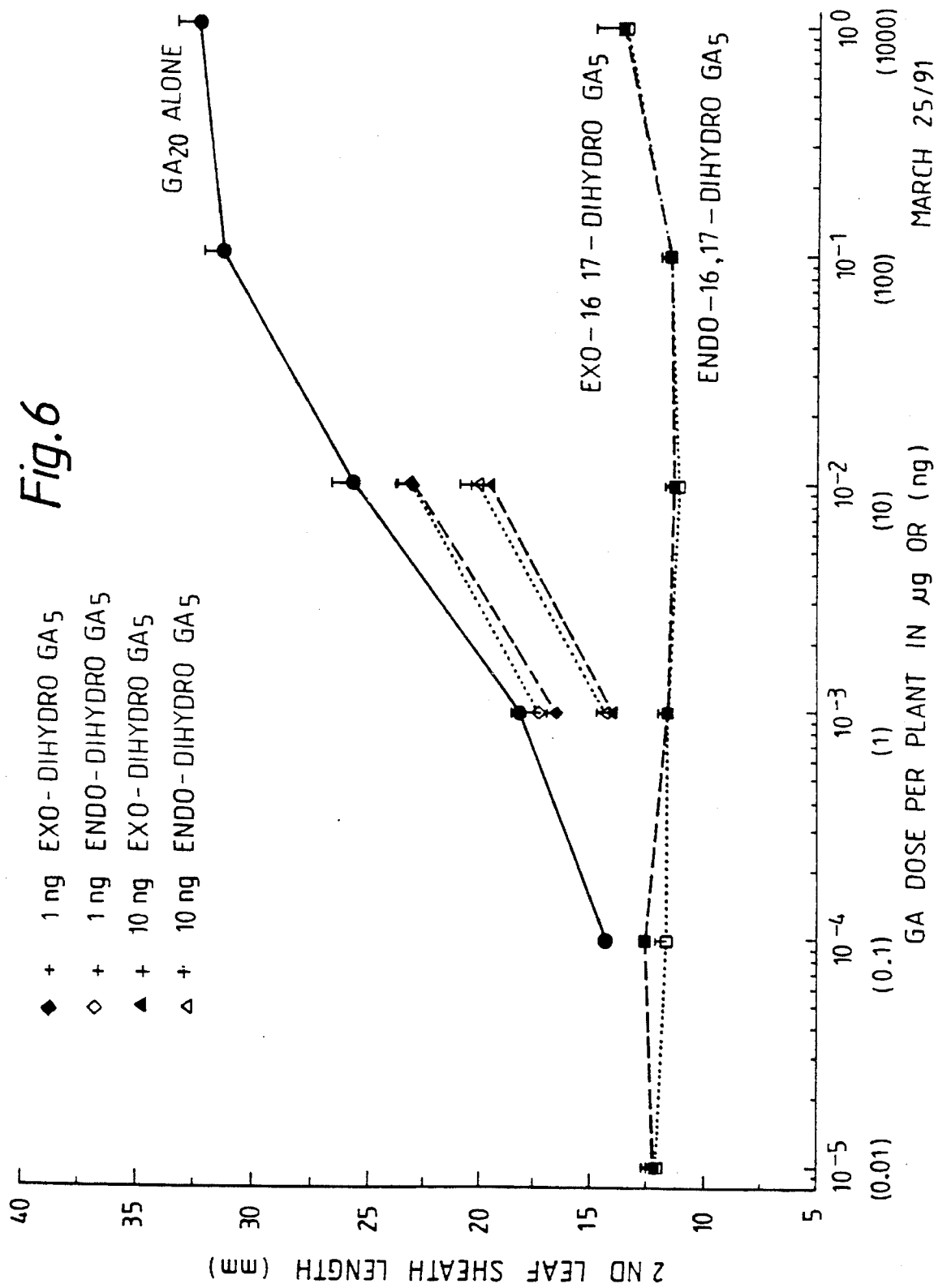
Figure 7:
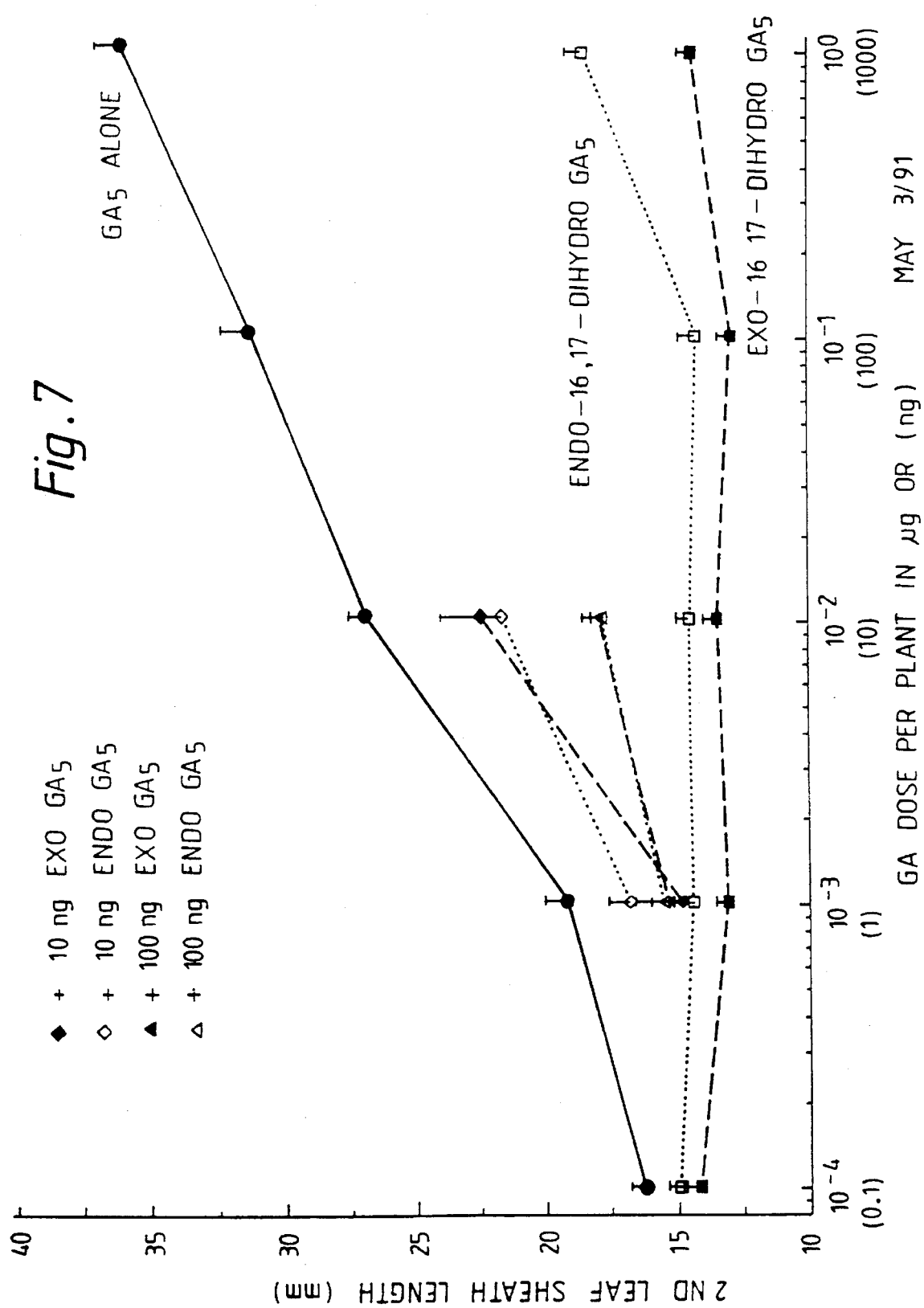

The results in FIGS. 3 and 4 show that diversion of stored carbohydrate into root and shoot is significantly diminished, which is of practical advantage to the brewer/malter

EXAMPLE 4

Retardation of Shoot Growth in Tan-Ginbozu Dwarf Rice

Uniconazole-treated rice plants of the dwarf variety Tan-ginbozu were treated with the following gibberellins:

$GA_5$, $GA_{20}$ or $GA_9$ endo-16,17-dihydro $GA_5$ exo-16,17-dihydro $GA_5$ exo-16,17-dihydro $GA_9$ Treatment rates varied from 0.01 to 1000 ng per plant for endo and exo-16,17-dihydro $GA_5$, from 0.1 to 100 ng/plant for $GA_5$ and from 0.1 to 1000 ng for $GA_9$ and $GA_{20}$.

The results are shown in FIGS. 5, 6, and 7, 7A 8 9 and 10 from which it can be seen that for both endo- and exo-16,17 dihydro $GA_5$, essentially no stem elongation effect is observed (c.f. $GA_5$ and $GA_{20}$), and further that both of endo- and exo-forms of dihydro $GA_5$ will significantly reduce (FIGS. 5,6,7 and 7A) the $GA_5$- or $GA_{20}$-induced growth promotion in the rice seedling. The exo-form of dihydro $GA_5$ is the least growth promotive at high doses (FIGS. 5, 7, 7A, 9 and 10) and also is significantly more growth inhibitory when tested versus $GA_5$ (FIG. 5), $GA_{20}$ (FIGS. 6 7A) and $GA_9$ (FIG. 9) although the relative effects of exo- vs. endo-forms varies with dose of the dihydro gibberelin and according to which of dihydro gibberelin is used. $GA_5$ and $GA_{20}$ are proven precursors to the effector gibberellins, $GA_3$ and $GA_1$ respectively.

Figure 8:
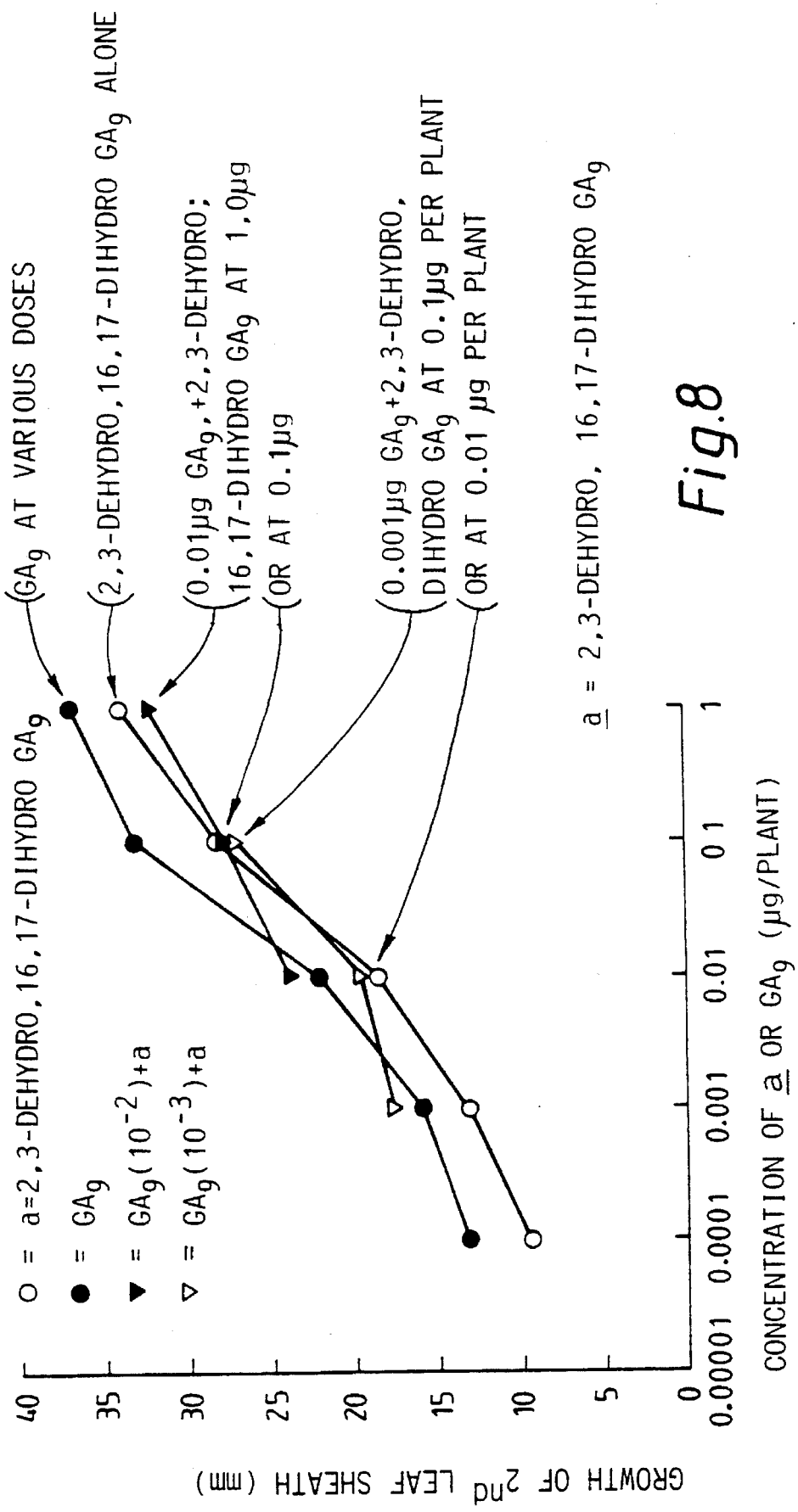
Figure 9:
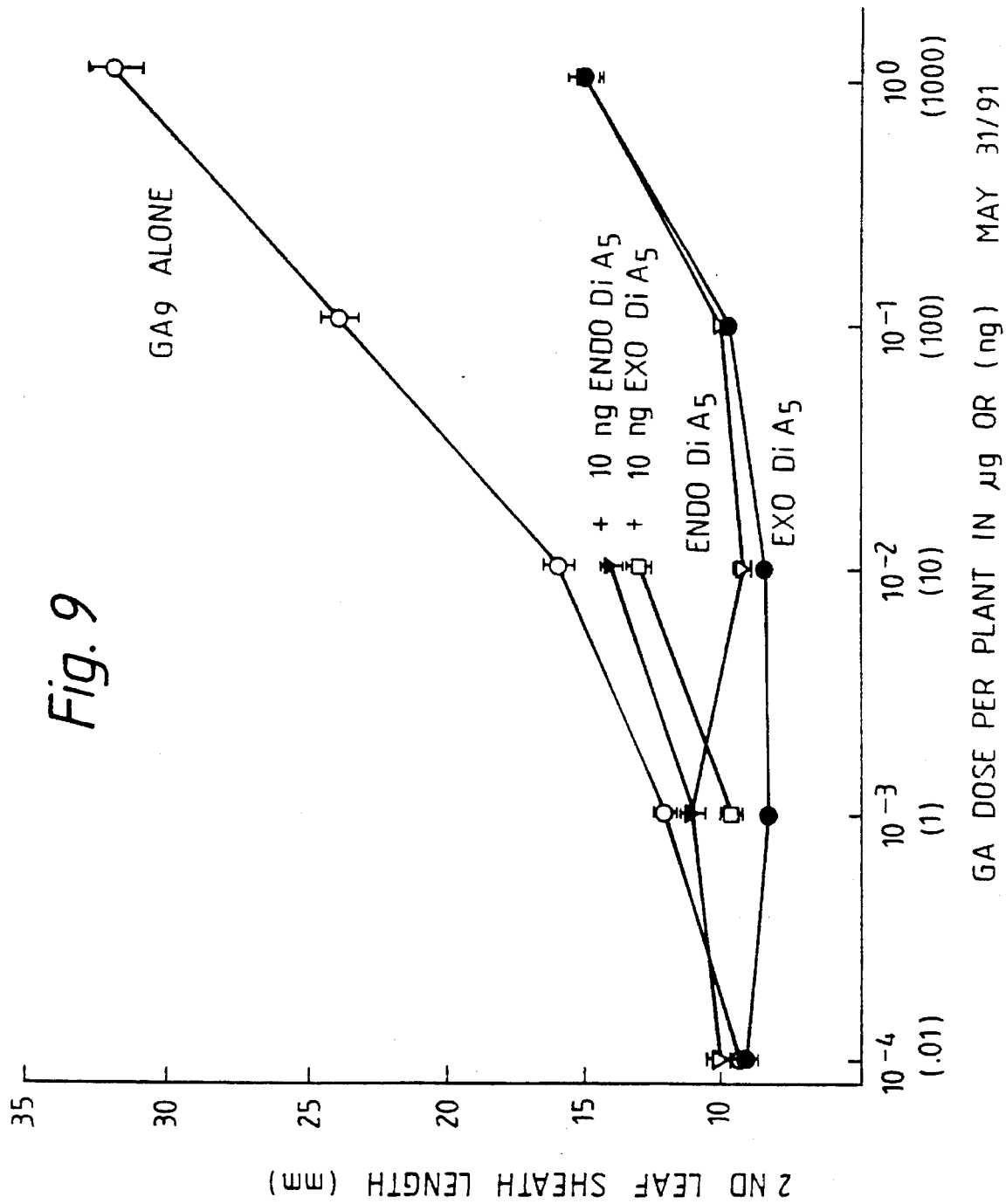
Figure 10:
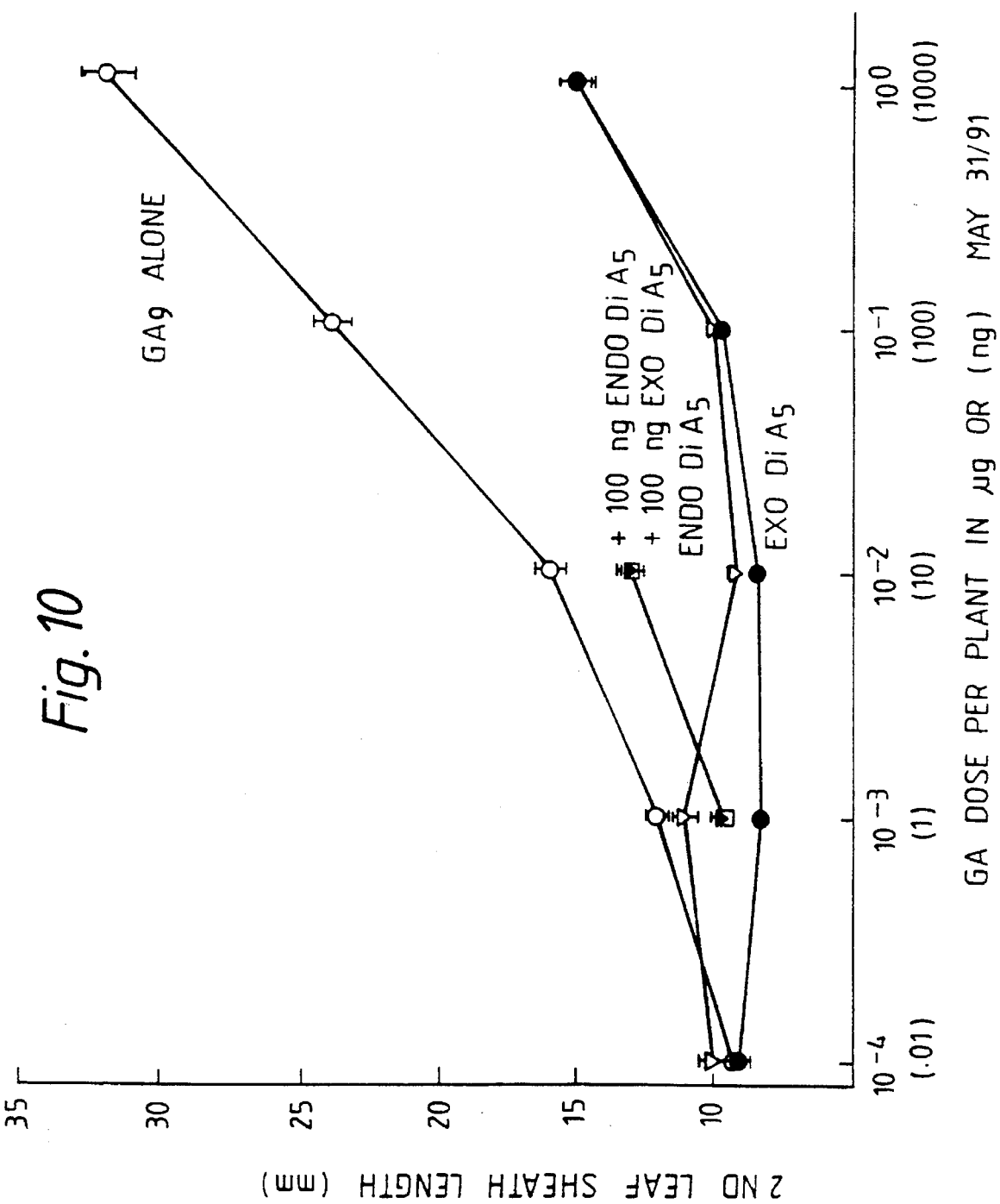
Figure 11:
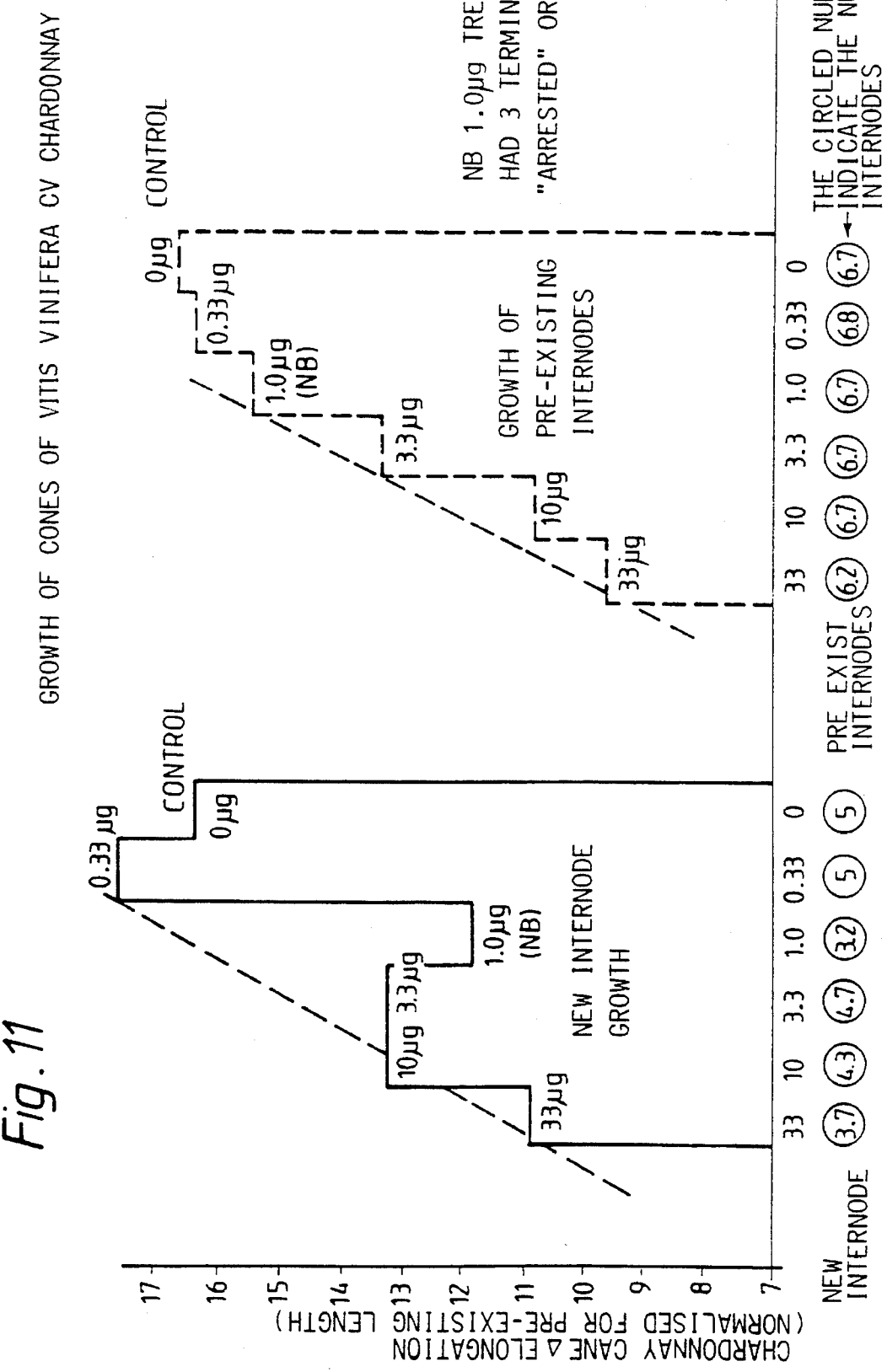
FIG. 11 shows the growth of cones of vitis vinifera.

The effect of 2,3-dehydro C-16,17-dihydro $GA_9$ was also tested against $GA_9$ on uniconazole-treated dwarf rice cv Tan-ginbozu, as were endo- and exo- forms of 16,17-dihydro GA5 (FIGS. 8, 9 and 10).

The results show:

I. 2,3-dehydro, C-16,17 dihydro GA9 alone (FIGS. 8, 9 and 10)

2,3-dehydro, c-16,17 dihydro $GA_9$ alone is quite active, but still less active than $GA_9$ alone (e.g. roughly 100 ng of the dihydro required to yield same growth promotion produced by 30–50 nanograms of $GA_9$).

II. 2,3-dehydro, C-16,17-dihydro $GA_9$ vs $GA_9$ (FIG. 8)

A. at lower concentrations of the dihydro $GA_9$ derivative there is a modest growth promotion, relative to $GA_9$ alone.

B. at higher concentrations of the dihydro $GA_9$ derivative there is modest to significant (statistically significant) inhibition of growth, relative to $GA_9$ alone (but there is still very good growth). C-16,17-dihydro $GA_5$ versus $GA_9$ also gave a modest but highly significant growth retardation (relative to $GA_9$ alone) at the higher doses of $GA_9$ (FIGS, 9 and 10).

Relatively speaking, C16,17-dihydro $GA_5$ appears to be a better antagonist than C-2,3 dehydro 16,17 dihydro $GA_9$ of $GA_9$-promoted growth in rice, possibly because the 3β-hydroxylase enzyme requires that the C-13 hydroxyl group be present on the dihydro GA molecule for good "recognition".

EXAMPLE 5

Cane Growth in Chardonnay Grape

The growth (Feb. 5th–Feb. 20th 1991) of Canes of *Vitis vinifera*, variety "Chardonnay", in response to a single application of 16,17-dihydro GA5 on Feb. 8th 1991, microdrops applied to tip and to each of 9 potential flower buds at each node. Average of 6 (usually) or 5 canes.

From the results in FIG. 9 it can be seen, compared to the controls both the new internode growth and growth of pre-existing internodes showed a strong and significant ($P \leq 0.05$) negative log-linear correlation with the applied dose of 16,17-dihydro $GA_5$ Dissection of two of the buds (Nos. 3 and 7 from the tip) has shown no inhibition of flower bud numbers by the treatment with 16,17-dihydro $GA_5$.

It can thus be concluded that application of $GA_5$ to *Vitis vinifera* cv Chardonnay significantly retarded cane growth without inhibiting flowering.

EXAMPLE 6

Retardation of Stem Elongation in Oilseed Rape

The degree of stem bolting in oilseed rape (W canola) in response to applied $GA_1$, $GA_5$ and 16,17-dihydro $GA_5$ was determined.

Figure 12:
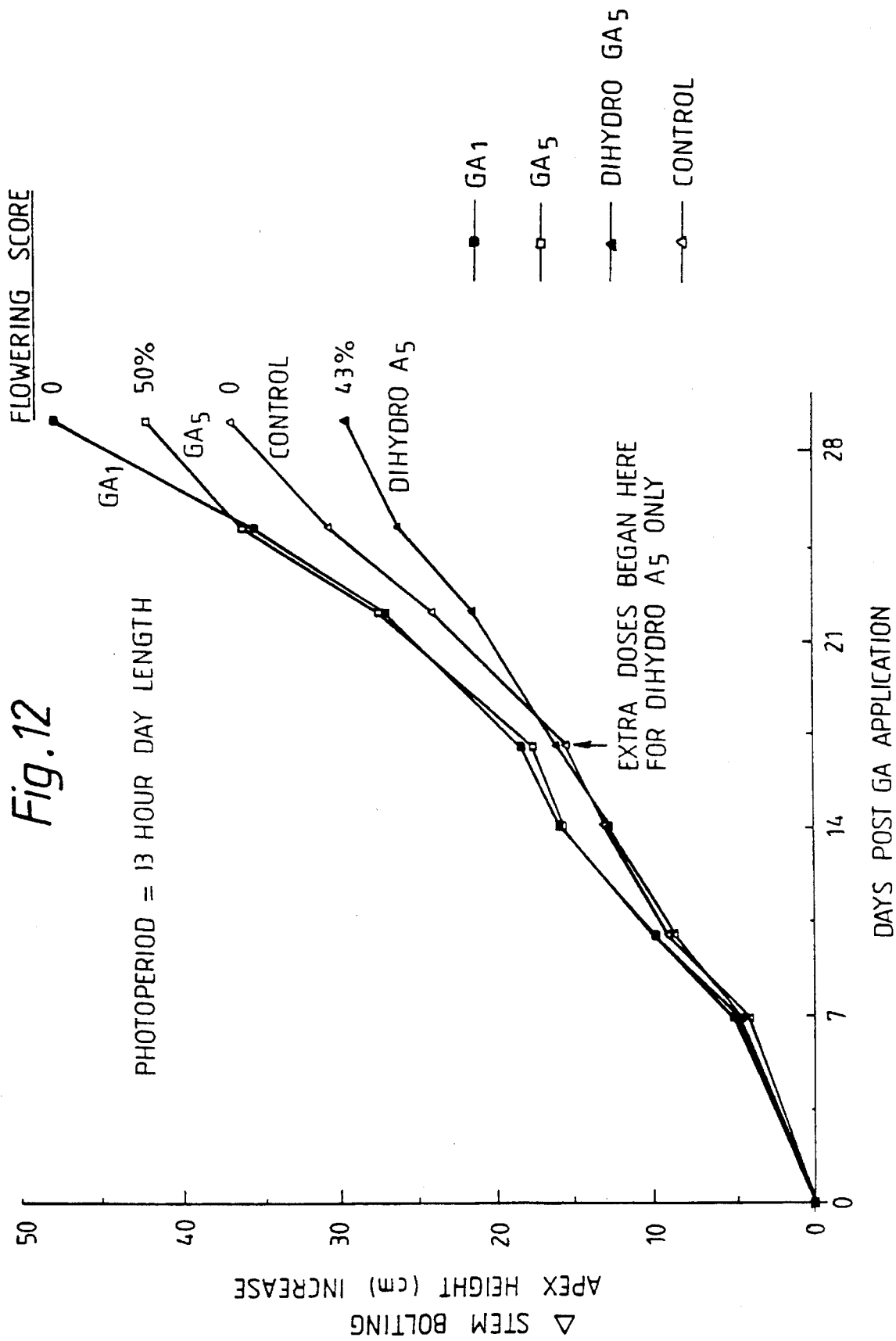
FIGS. 12 and 13 show that both GA1 and GA5 produced the expected promotion or stem elongation typical of effector gibberellins.
Figure 13:
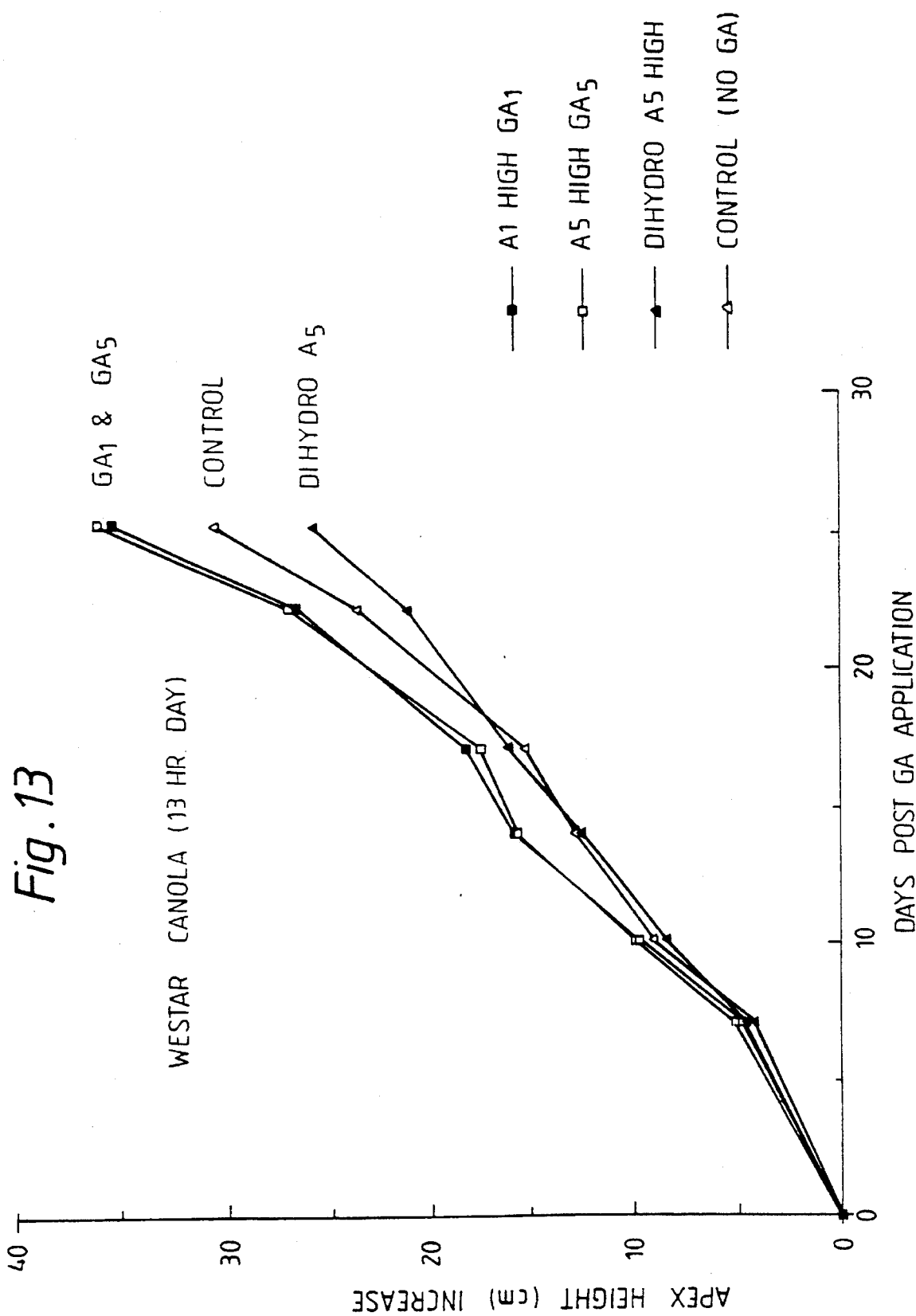

From the results in the accompanying FIGS. 12 and 13 it can be seen that both $GA_1$ and $GA_5$ produced the expected promotion or stem elongation typical of effector gibberellins.

Dihydro $GA_5$ however produced a significant reduction (FIGS. 12 and 13) in the degree of stem elongation (stem bolting) while still promoting (FIG. 12) floral stage development almost as well as $GA_5$ ($GA_1$ did not promote floral stage developement) flowering.

EXAMPLE 7

Bud Break—M Pohutakawa

The effect of C-16,17-dihydro $GA_5$ (specifically C-16,17-dihydro $GA_5$) on bud break was assessed on a shrub of the Myrtaceae family (Meterosideros Pohutakawa). Retardation of bud break in fruit trees, shrubs and forest trees is useful to prevent damage from late frosts, and to synchronise flowering in grapes, And in potted shrubs for the florist trade.

The results were as follows:

| Treatment | Proportion of Buds Broken Dormancy at | | |
|---|---|---|---|
| | Day 10 | Day 75 | Day 97 |
| Control | 42% | 73% | 94% |
| 1 ppm C-16,17-dihydro $GA_5$ | 21% | 75% | 89% |
| 10 ppm C-16,17-dihydro $GA_5$ | 34% | 55% | 61% |
| 100 ppm C-16,17-dihydro $GA_5$ | 21% | 27% | 33% |

Thus C-16.17-dihydro $GA_5$ effectively retarded bud break relative to controls.

EXAMPLE 8

Herbicidal Effect on Wild Oats

Durhum wheat infested with wild oats was treated with C-16,17-dihydro $GA_5$ at a treatment rate of 33 ppm and 100 ppm.

Figure 14:
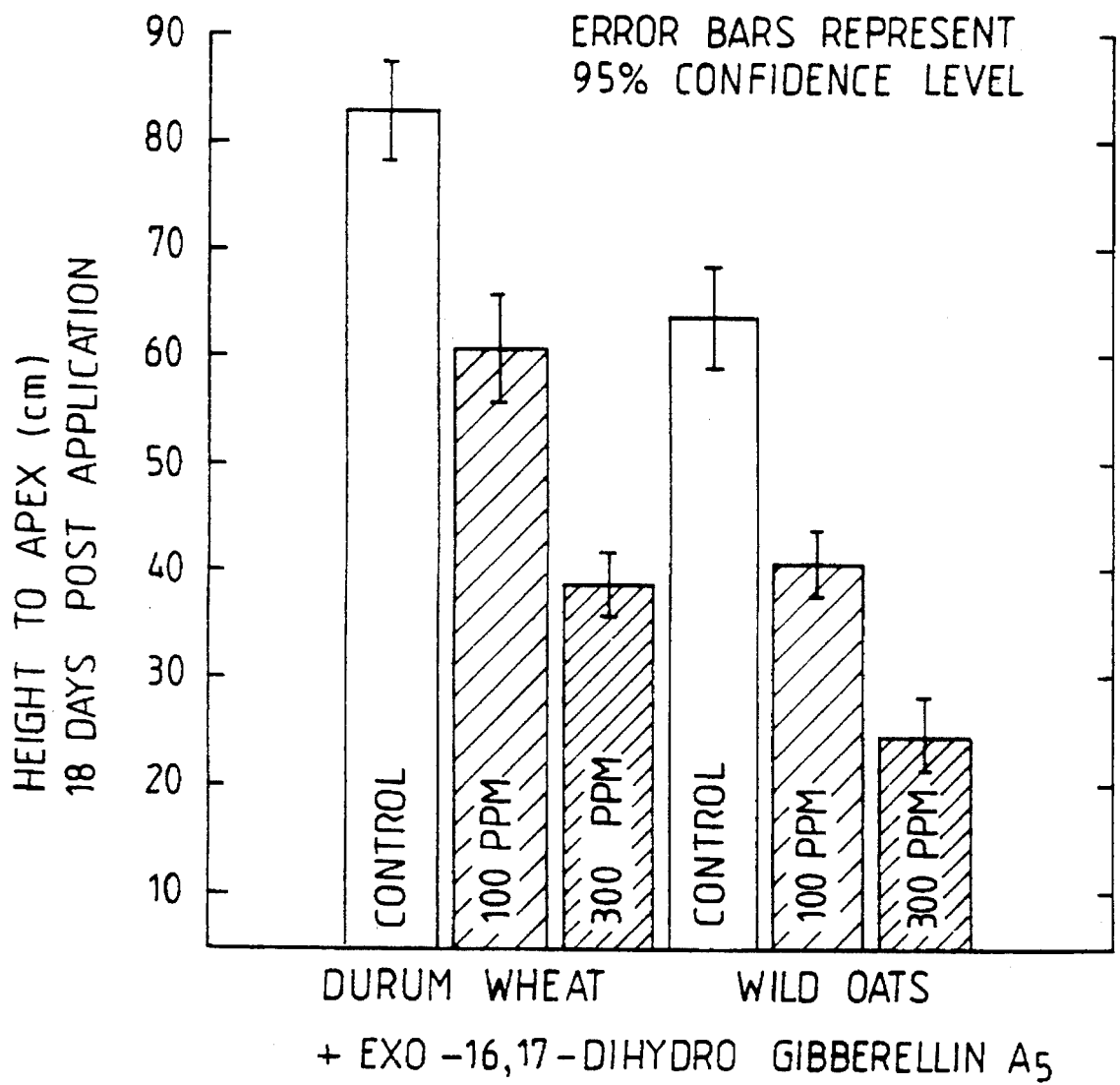
FIG. 14 shows that growth of wild oats was retarded significantly by application of C-16,17-dihydro GA5.
Figure 15:
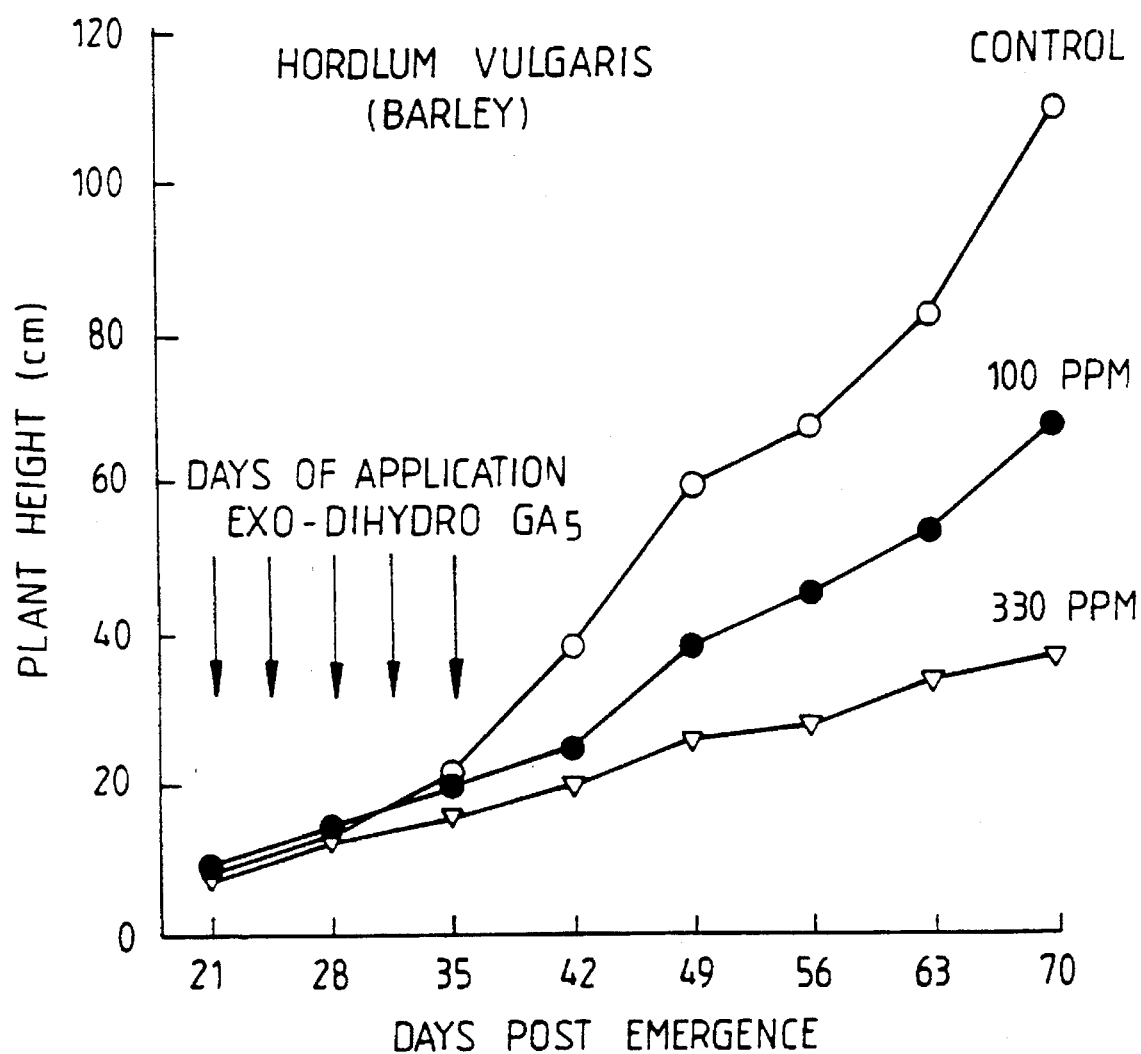
FIG. 15 shows the effect of exo-dihydro $GA_5$ on barley height.
Figure 16:
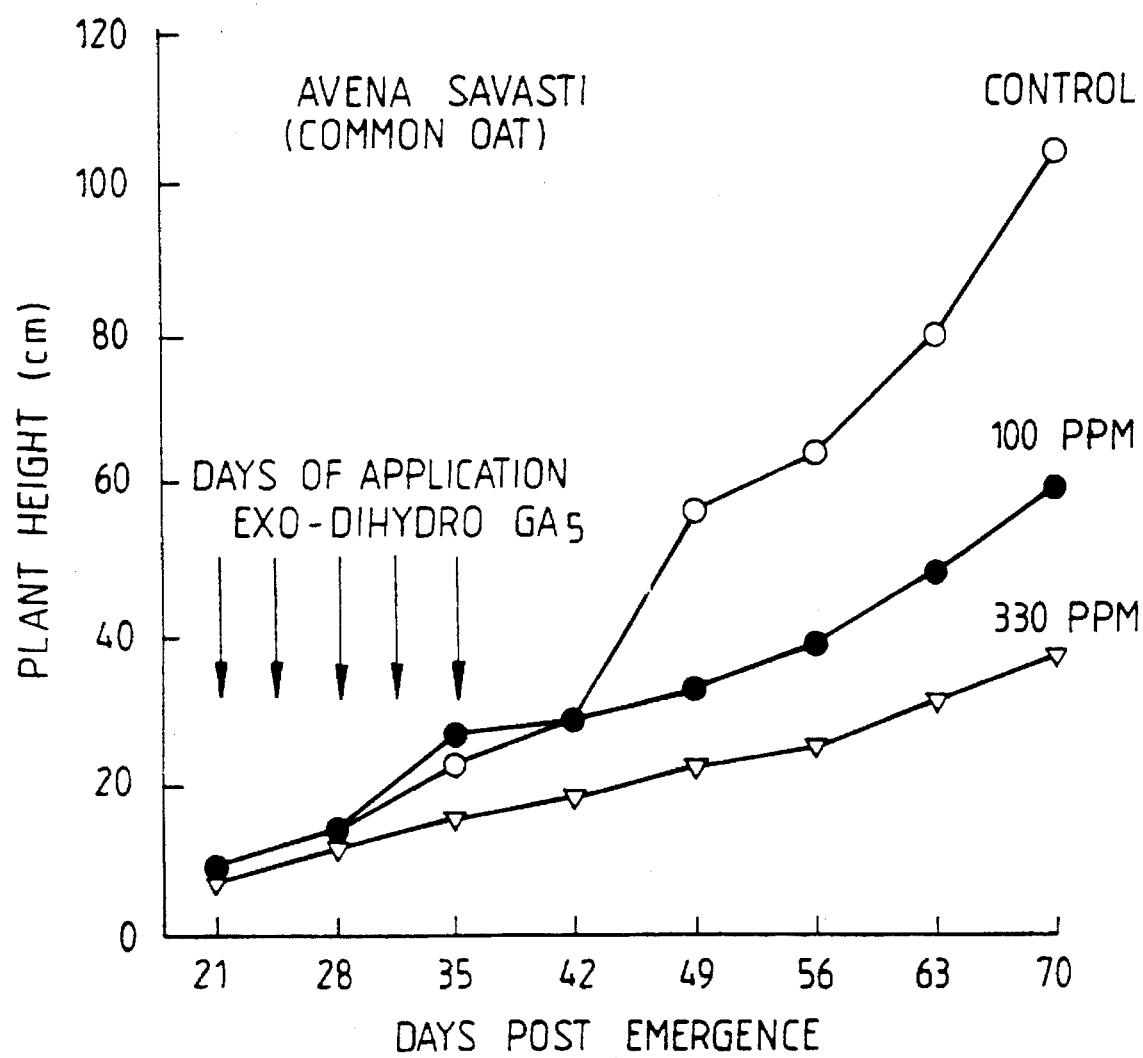
FIG. 16 shows the effect of exo-dihydro $GA_5$ on common oat height.
Figure 17:
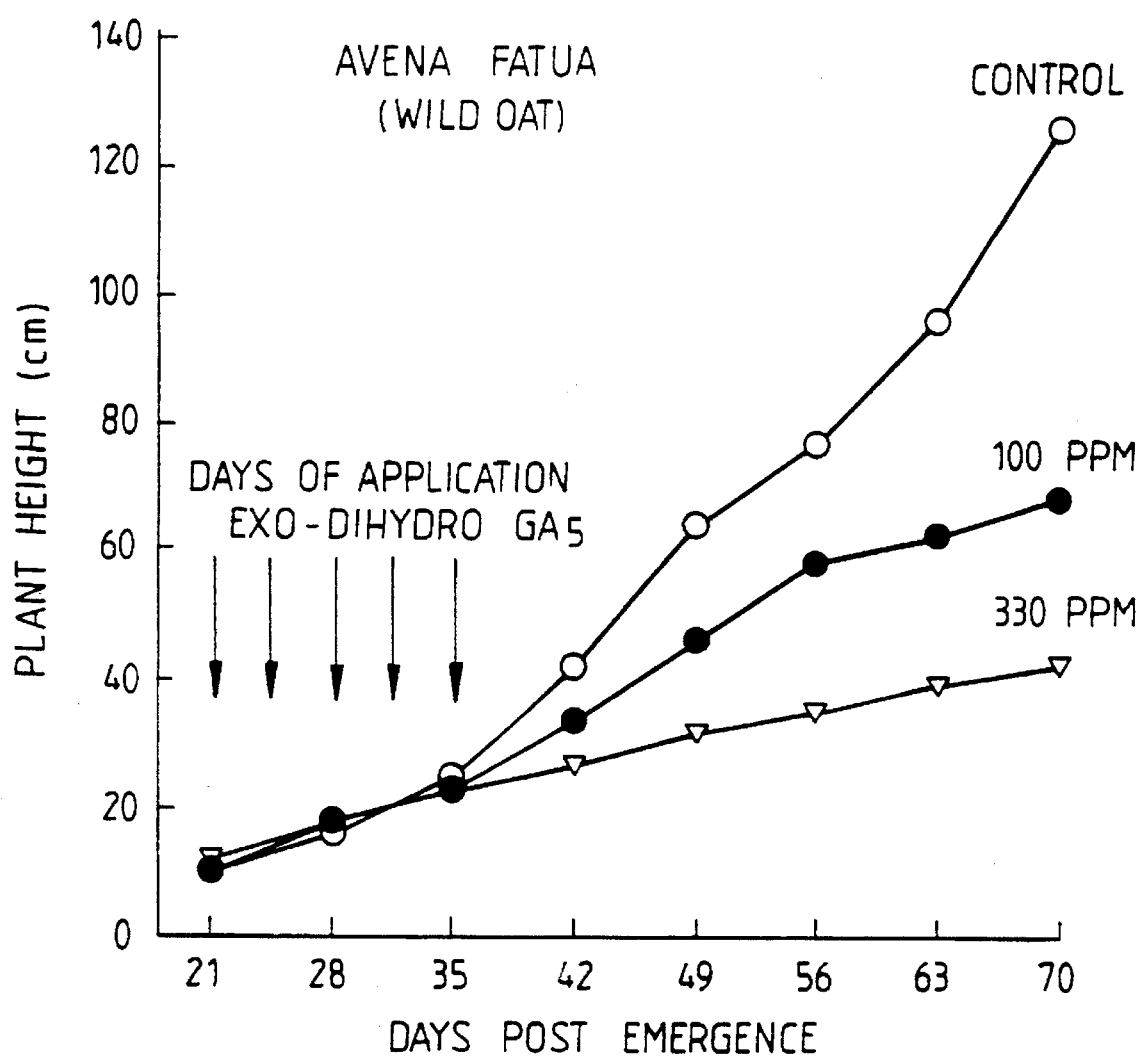
FIG. 17 shows the effect of exo-dihydro $GA_5$ on wild oat height.

The results are shown in FIG. 14 from which it can be seen that the wild oats werre retarded significantly. The Durham wheat was retarded (a desirable effect) but appeared normal and dark green and flowered normally although a day or two delayed. Evidence was also seen of a yellowing and toxicity in the wild oat infestation.

EXAMPLE 9

Promotion of Male Cone Buds

A. C-16,17 dihydro GA5 was applied at pre-bud swell stage of development in 1991 to Douglas fir clonal propagules (used for seed production). Male flowers (conebuds) were assessed in spring, 1992 for endo- or exo- C-16,17 dihydro GA5 applied.

The results were as follows:
1. endo-C-16,17 dihydro GA5 0,0,13,0,0,2,0,0=1.88 male conebuds/treated propagule
2. Control 0,0,8,0,0,0,0,0=1.0 male conebuds/treated propagule
3. exo-C-16,17 dihydro GA5 4,0, -, 1,0,0,0,=0.7 male condbuds/treated propagule
4. Control 0, ,4,0,1.0,0,0,=0.8 male B. C-16,17 dihydro GA5 was applied at vegetative bud break stage of development in 1991 male flowers (conebuds) were assessed in spring, 1992 for endo- or exo- C-16,17 dihydro GA5 applied to Douglas fir clonal propagules (used for seed production in seed orchards).

Treatment branches were chosen for the likelihood that male flowers (conebuds) would be produce (e.g. low branches).

There were almost no female flowers (conebuds produced).

The results were as follows
1. endo-C-16,17 dihydro GA5 20, 6, -, -, -, -,=4.33 male conebuds/treated propagule (- -=branch died)
2. Control 13, 2, -, -, -, -=2.5 male conebuds/treated propagule
3. exo-C-16,17 dihydro GA5 0, 10, 0,0,0,-=1.4 male conebuds/treated propagule (0=no male flowers (conebuds))
4. Control 0,6,0,0,0,-,-,0,=1.0 male conebuds/treated propagule There were essentially no female flowers (conebuds) produced on the chosen branches of these propagule.

EXAMPLE 10

Inhibition Seed Set or Production/Induction of Tillering

Sprays of exo- dihydro GA5 were made up in 1% activator (surfactant) at each of 0, 100 ppm and 330 ppm, and sprayed to "drip off" to each of:

oat (domestic—*Arena savasti*, common oat)

wild oat (weed)—*Avena fatua* barley (*Hordeum vulgaris*)

The plants were planted in trays, emergence occurred within 3 to 5 days of planting.

Photoperiod was 16 hours, temperature regime was 24° C. during the 16 hr day, and 18° C. during the 8 hr night. These are "long days" under which growth is rapid, and flowering will normally occur.

FIGS. 15 to 18 showing plant height (cm) are attached for each species.

It can be seen that the highest dosage (330 ppm) gave a growth (final height) of only 35 to 40 cm. Height on the 330 ppm treatment was obtained by measuring the length of the longest/tallest leaf. The appearance was one of "lawn grass", and no flowering occurred (based on observations on day 70, when seed counts were made on other treatments (see FIG. 18), and apices were dissected out on the 330 ppm treatment to see if flowering had been initiated).

But when sprayed at 330 ppm gave no flowering al all (plants were dissected, no floral apices were apparent).

Observations were made as follows:

Day 49

Inflorescence heads observed on a few barley and wild cat plants for the first time (control plants only).

Domestic oat plants did not show inflorescences, but there was a swelling that could be felt, indicating that the inflorescence is "present in the boot" (again, control plants only).

100 ppm plants were shorter than controls, with no visible inflorescence heads.

330 ppm plants were more stunted than the 100 ppm plants.

Day 56

For control plants inflorescence heads were observed on all species, with wild oats being the most developed.

100 ppm dihydro GA5 (exo-) inflorescence heads were observed on all species, but size of inflorescence head and of the plant per se was reduced, relative to Control.

330 ppm dihydro GA5 (exo-)—no inflorescence heads observed on any species, over all size of plant is very reduced.

Day 63

Control plants of all species had normal head development, with heads filled or filling with seeds. Wild oat are most advanced, and lowest seeds are beginning to ripen.

100 ppm dihydro GSA5 (exo-) shorter than control (see Figures), but some seed set had obviously occurred. Head size is reduced in comparison with Control.

330 ppm dihydro GA5 (exo-) show no heads, very little growth (see Figures). All plants have wide (wider than controls) dark green leaves.

Day 70

Harvest and Seed count.

I. Inhibition of Seed Production

Control plants looked "normal", with average size heads, filled with seed.

100 ppm dihydro GA5 (exo-) treated plants were reduced in size, and a number of glumes (common name is "houses") were empty (e.g. either sterile, or aborted—see bar graph showing; reduced number of seeds/plant for the 100 ppm treatment).

330 ppm dihydro GA5 (exo-) showed very reduced height, no floral development, hence no seeds (see bar graph).

In essence, 330 ppm exo- dihydro GA5 yielded semi-prostrate plants that gave an appearance of lawn grass.

Not only was seed set/production prevented, but flowering was prevented (presumably due to absence of endogenous "effector gibberellin" caused by the dihydro GA5 blocking the biosynthetic 3β-hydroxylation "activating" step (e.g. blocking GA20 —>1 or GA20—>GA5—GA3).

This experiment also shows that the dose is related to the desired effect, since 100 ppm only partially reduced seed production (see FIG. 18), whereas 330 ppm completely eliminated seed production by preventing flowering.

II. The promotion of Tillering

The promotion of tillering (producting of lateral buds, which form additional shoots in grain species by application of the exo- form of C-16,17 dihydro GA5 was assessed.

Additional tiller shoots may be practically useful for additional grain yield if the tillers can be produced early on, and thus allow for extra spike and seed production/plant.

Gibberellin A3, a known "effector" of elongation growth to species of Graminae, including commercially important grain species, is known to enhance apical dominance, thereby reducing or preventing tillering (see M. A. Harrison and P. B. Kaufman, 1980, Plant Physiology 66:1123—1127 and references cited therein).

Therefore it is surprising that a gibberellin such as C-16, 17 dihydro GA5 (exo- isomer), when applied to a grain species (such as barley, the example given) would actually promote tillering (see Tables 1 and 2), rather than inhibiting it as does applied GA3.

However, a possible explanation is that applied C-16,17 dihydro GA5 will inhibit the production of endogenous "effector" gibberellin-A1 and gibberellin A3, thereby allowing the main caulm to lose apical dominance control of its lateral buds, which then begin to grow out and develop, yielding 1 or more additional tiller shoots on each plant.

EXAMPLE 11

Co-Application of Dihydro Ga5 With Ethephon

C-16,17 dihydro GA5 (exo- form) was dissolved in ethanol, water added as was Activator surfactant (0.1%) to make a final concentration of 330 ppm in 10% ethanolic solution.

Spray was to "drip-off" and three treatments were used: weekly beginning at 21 days after sowing, ending 5 weeks (5 applications) later.

as above, but plus 40 milli-molar ethephon (an ethylene releasing compound) which also retards growth in barley and promotes tiller formation)

one application of C-16,17 dihydro GA5 at Zadoks Growth Stage 43+ethephon as noted above The results are shown in the attached Table 1 (plant height and internode length) and Table 2 (production of early and late tillers and flowering).

With regard to tiller production it is apparent from Table 2 that use of C-16,17 dihydro GA5 (exo- form) significantly promotes the number of early sterile tillers (2.8) relative to control (0.7), and very significantly promotes the number of late tillers (pre-flowering at time of assessment), 7.8 or 7.1 tillers (5 applications of C-16,17 dihydro GA5 or one application of C-16,17 dihydro GA5+ethephon, respectively, relative to control (1.6 tillers).

That the early tillers are sterile is undoubtedly due to the high dose used. A lower dose/frequency of C-16,17 dihydro GA5 should promote tillering while still retarding shoot growth, but with good seed set (for example see FIG. 18; 100 ppm dosage).

In Table 2 treatment with 5 applictions of C-16,17 dihydro GA5 significantly reduced fertile florets to 3 per spike (control was 34 or 42), and significantly promoted sterile florets to 50 per plant (control was 11 or 13).

Treatment with 1 application of C-16, 17 dihydro GA5+ ethephon very effectively reduced number of florets to 1 per spike, and increased sterile florets to 57 per spike.

Hence, Table 2 shows evidence of very reduced fertility (virtual lack of seed production) from 5 times application of C-16,17 dihydro GA5, and an exceptionally reduced fertility with one application of C-16,17 dihydro GA5+Ethephon.

This would yield a herbicide effect by effectively limiting the production of seed in weeds in the Graminae Order, and would thus have practical uses in crops of dicotyledenous species (such as rapeseed) whereby production of weed seed (such as wild oats) could be eliminated.

Height reduction by C-16,17 dihydro GA5 is also shown in Table 1, either by 5 applications of the dihydro GA5 alone, or by one application of dihydro GA5+ethephon. Both were very significant retarders of height, and data from Table 1 could be useful as an example of plant growth retardation by dihydro GA5.

EXAMPLE 12

Inhibition of Seed Set in Barley

Barley was grown in autumn 1991 in high intensity light supplemented heated glasshouses.

Treated plants received:

exo- isomer of C-16,17 dihydro GA5 at:
0 (Control)—0 ppm
$1.0 \times 10^{-4}$ (minus 4) molar spray—35 ppm
$3.3 \times 10^{-4}$ (minus 4) molar spray—116 ppm
$1.0 \times 10^{-3}$ (minus 3) molar spray—350 ppm applied initially to the barley plants at the three-to-four leaf stage.

In some experiments only one application was given, in other experiments 3 applications were given, the 2nd application being applied one week after the initial application, the 3rd application being applied two weeks after the initial application.

There are two replicate experiments. The repeat experiment was staggered in time, but applications began at the same approximate stage (e.g. three to four leaf stage). Hence, variability due to replicate experiments may be due to random variation, or to differences in weather (e.g. overcast for 10 days in one trial, those days being at a different stage of development in the repeat trial).

The index of sterility (male and/or female) is seed yield/ plant, expressed in each of weight of kernels (grams) produced per plant and volume of grain produced per plant.

Similarly, the efficacy as a herbicide treatment (e.g. prevention of seed production) is seed yield/plant, expressed in each of weight of kernels (grams) produced per plant and volume of grain produced per plant.

|  | Control | 35 ppm | 116 ppm | 350 ppm | P value |
|---|---|---|---|---|---|
| Test #A. cv. Leduc Barley Single Spray | | | | | |
| Kernel Wt (grams), | 0.92a | 0.77a | 0.64ab | 0.33b | 0.0108 |
| Kernel Volume (ml) | 4.75 | 4.00 | 3.25 | 2.50 NS | 0.5699 |

Note: Different letters Connote Significant Difference Between Treatments
NS = No Significant Difference Between Treatments

| Test #B. cv. Leduc Barley (Repeat of Test #A) Single Spray | | | | | |
|---|---|---|---|---|---|
| Kernel Wt (grams) | 1.09a | 1.19a | 0.99a | 0.44b | 0.0157 |
| Kernel Volume (ml | 5.00 | 5.50 | 5.00 | 2.31 NS | 0.0897 |

Note: NS = No Significance Between Treatments Different letters Connote Significant Difference Between Treatments

| Test #C, cv. Leduc Barley Three Spray Applications | | | | | |
|---|---|---|---|---|---|
| Kernel Wt (grams) | 0.71a | 0.35b | 0.10c | 0.00c | 0.0015 |
| Kernel Volume (ml) | 3.25a | 1.31b | 0.38b | 0.00b | 0.0018 |

Note: Different Letters Connote Significant Difference Between Treatments

| Test #D. cv. Leduc Barley (Repeat of Test #C) Three Spray Applications | | | | | |
|---|---|---|---|---|---|
| Kernel Wt (grams) | 1.54a | 1.23a | 0.56b | 0.44b | 0.0160 |
| Kernel Volume (ml) | 7.33a | 5.50ab | 2.63b | 2.25b | 0.0424 |

Note: Different letters Connote Significant Difference Between Treatments

| Test #E, cv. Jackson Barley Single Spray | | | | | |
|---|---|---|---|---|---|
| Kernel Wt (grams) | 1.54a | 1.54a | 1.65a | 0.88b | 0.0001 |
| Kernel Volume (ml) | 8.50 | 9.75 | 9.25 | 5.50 NS | 0.0898 |

Note: NS = No Significance Between Treatments
a vs b = Significant Difference Between Treatments

| Test #F. cv. Jackson Barley (Repeat of Test #E) Single Spray | | | | | |
|---|---|---|---|---|---|
| Kernel Wt (grams) | 0.50 | 0.35 | 0.29 | 0.24 NS | 0.9363 |
| Kernel Volume (ml) | 1.01 | 0.76 | 0.50 | 0.13 NS | 0.4702 |

Note: NS = No significance Between Treatments

| Test #G. cv. Heartland Barley Single Spray | | | | | |
|---|---|---|---|---|---|
| Kernel Wt (grams) | 1.60a | 1.23b | 0.80c | 0.20d | 0.0001 |
| Kernel Volume (ml) | 6.175a | 31.23a | 3.50b | 1.00c | 0.0001 |

Note: Different letters Connote Significant Difference Between Treatments.

| Test #H. cv. Heartland Barley (Repeat of Test #G) Single Spray | | | | | |
|---|---|---|---|---|---|
| Kernel Wt (grams) | 0.61ab | 1.00a | 0.89a | 0.27b | 0.0312 |
| Kernel Volume (ml) | 3.03 | 4.50 | 4.00 | 1.40 NS | 0.0634 |

Note: NS = No significance Between Treatments Different letters Connote Significant Difference Between Treatments

CONCLUSIONS

Reduced Seed Production (e.g. sterility) occurs with increased dose of the exo- isomer of C-16,17 dihydro GA5.

In fact, in one test (#C, Leduc Barley), complete sterility (no seed production occurred).

EXAMPLE 13

Inhibition of Flowering; Prostrate Growth

Figure 18:
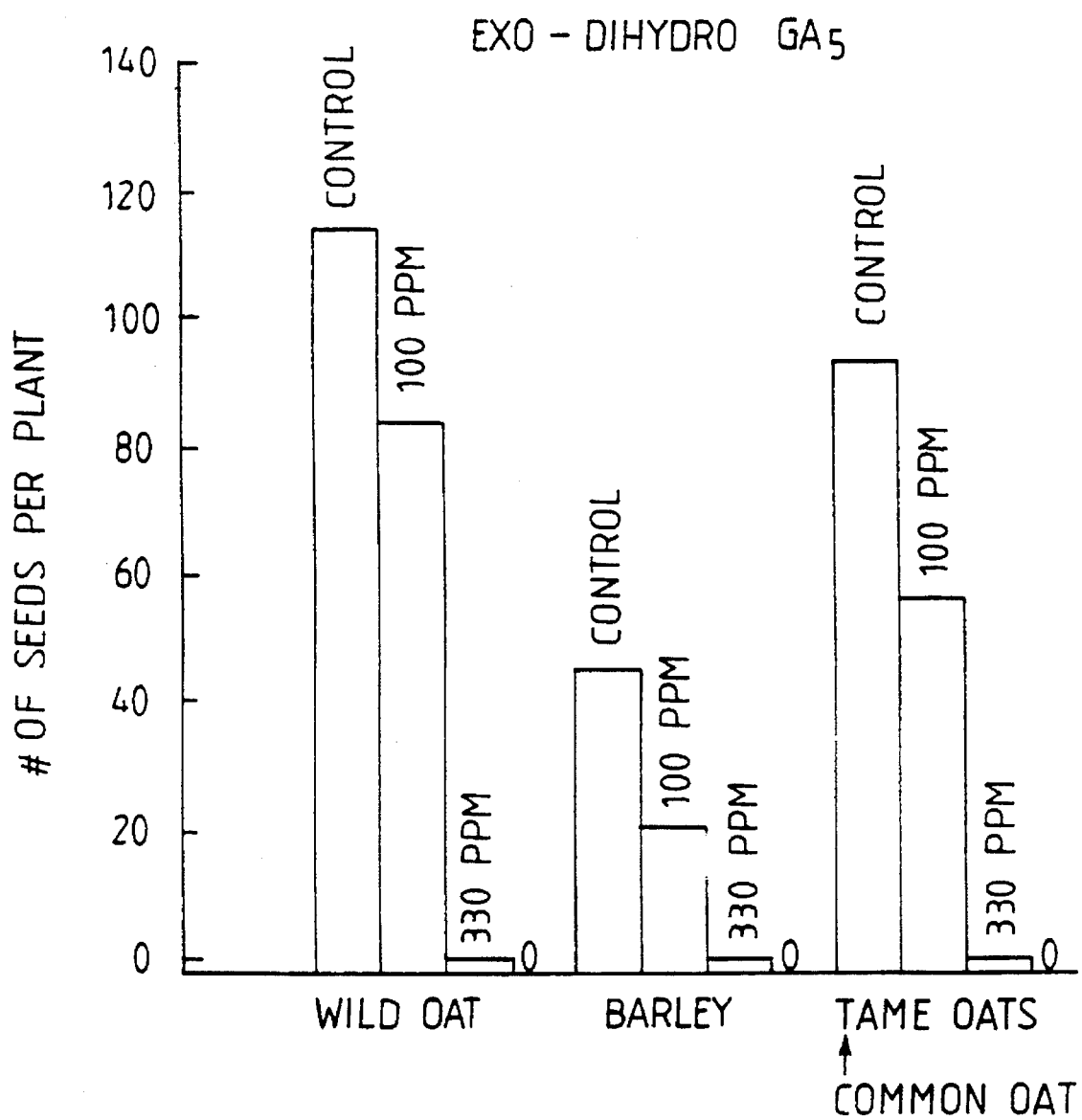
FIG. 18 shows the effect of exo-dihydro $GA_5$ on number of seeds per plant in oats and barley.

Dihydro GA5 (exo- form) was sprayed 5 times to each of:
oat (domestic)
wild oat (weed)
barley When sprayed at 100 ppm dihydro GA5 gave reduced height (FIGS. 15–17), but normal or near-normal seed set (FIG. 18).

When sprayed at 350 ppm gave no flowering at all (plants were dissected, no floral apices were apparent).

In essence, 350 ppm exo- dihydro GA5 yield prostrate plants that gave an appearance of lawn grass Not only was seed set/production prevented, but flowering was prevented (presumably due to absence of endogenous "effector gibberellin" caused by the dihydro GA5 blocking the biosynthetic 3β-hydroxylation "activating" step (e.g. blocking GA20—>GA1 or GA20—>GA5—GA3).

EXAMPLE 14

Herbicidal Effect—Wild Oats

Plant growth (wild oat plant growth) biomass data from the Summer 1991 trial (see Photographs 1–5) noted below provides additional evidence of a "herbicidal type of effect" of exoC-16,17 dihydro GA5 when applied to wild oat:

|  | WILD OAT | | |
|---|---|---|---|
|  | Control | 100 ppm | 300 ppm |
| Straw Weight/plant | 7.87 g | 5.39 g | 6.37 g |
| Straw Weight/3 square meters) | 2259 g | 1192 g | 1166 g |
| No. Plants/plot (Surviving plants) | 287 | 221 | 183 |

The above results demonstrate:

A. a reduction in surviving wild oat plants within the treated plots for a single spray of exo- dihydro GA5, 300 ppm being more efficacious than 100 ppm.

B. a reduction in biomass of wild oat straw (e.g. everything except the seed) yo 68% of control for 100 ppm, and 81% of control for 300 ppm per plant.

C. a reduction in biomass per unit area (e.g. per acre, per hectare) to ca. 50% of control, 100 and 300 ppm being about equal.

The above effects on wild oat are very much more pronounced than on durum wheat, for which the results are given below:

|  | WHEAT DURUM | | |
|---|---|---|---|
|  | Control | 100 ppm | 300 ppm |
| Straw Weight/plant | 5.92 g | 4.69 g | 4.68 g |
| Straw Weight/plot | 870 g | 737 g | 660 g |
| No. Plants/plot (Surviving plants) | 147 | 157 | 141 |

EXAMPLE 15

An Effect of Different Dosage on Retarding the Stem Elongation of Barley CV Leduc 1991–2 glasshouse trial using Leduc barley.

Barley grown in autumn 1991 in high intensity light supplemented heated glasshouses. Treated plants received:

exo- isomer of C-16,17 dihydro GA5 at:
- 0 (Control)—0 ppm
- $1.0 \times 10^{-4}$ (minus 4) molar spray—35 ppm
- $3.3 \times 10^{-4}$ (minus 4) molar spray—116 ppm
- $1.0 \times 10^{-3}$ (minus 3) molar spray—350 ppm applied initially to the barley plants at the three-to-four leaf stage.

In some experiments only one application was given, in other experiments 3 applications were given, the 2nd application being applied one week after the initial application, the 3rd application being applied two weeks after the initial application.

The results are shown in the accompanying FIGS. 19 to 26.

Figure 19:
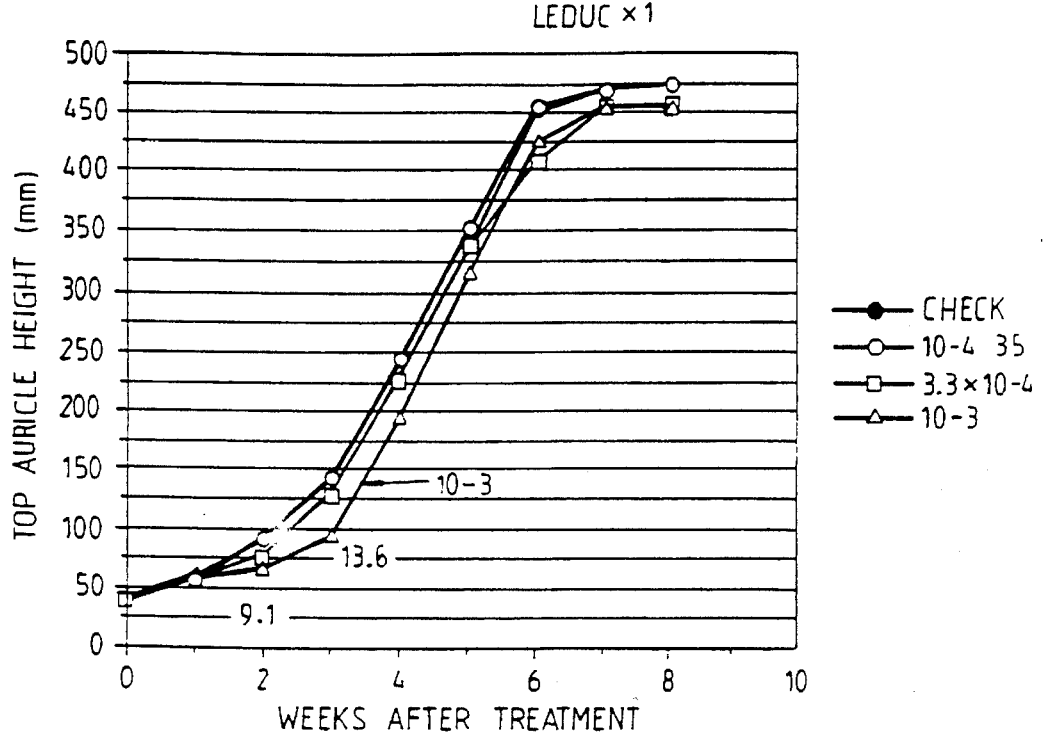
Figure 20:
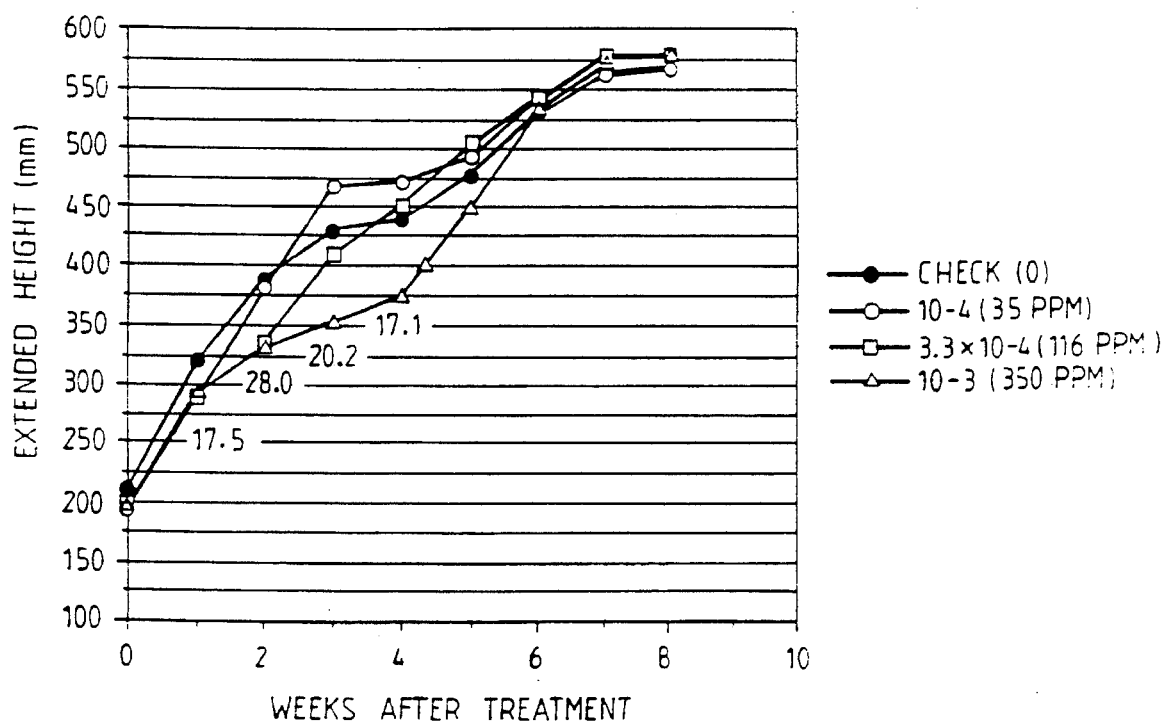

FIG. 19 shows the response to a single spray application (Leduc×1), FIG. 21 showing the response to 3 spray applications.

For extended height (mm) especially, dose response differences are apparent for both the single spray (Leduc×1) and especially for the 3× spray (Leduc×3).

Similarly to the top of the auricle (the leaf which shelters the grain head) the 3 times application (Leduc×3) shows a very marked (and significant) difference with differing dose, 116 ppm and 350 ppm, especially being quite growth retardive.

Thus, the figures show:

a dose response from 0 to 350 ppm (higher dose is most growth retardive)

a frequency response (higher frequency is most growth retardive).

TABLE 1

Plant height and internode lengths following applications of ethephon and EDHGA5* separately and together to greenhouse grown Bonanza barley

| Treatment | n+ | Plant Height cm | Peduncle cm | Internode $P^{-1}$ cm | $P^{-2}$ cm | $P^{-3}$ cm | $P^{-4}$ cm | n | $P^{-5}$ cm | n | $P^{-6}$ cm |
|---|---|---|---|---|---|---|---|---|---|---|---|
| Control | 21 | 100a | 28.3a | 17.0a | 12.3ab | 11.1b | 7.4c | 21 | 5.3a | 8 | 1.4 |
| Activator | 23 | 101a | 24.8b | 17.7a | 13.2a | 12.2a | 8.7a | 22 | 6.0a | 8 | 2.0 |
| Ethephon | 22 | 67b | 9.5d | 6.7bc | 11.1bc | 11.9ab | 8.4ab | 22 | 5.1ab | 6 | 2.3 |
| Ethephon + Activator | 24 | 65b | 10.0d | 6.8bc | 9.9c | 11.1bc | 8.6a | 24 | 5.1ab | 13 | 1.5 |
| EDHGA5 (weekly) | 26 | 57c | 16.3c | 7.7b | 4.8d | 3.5d | 2.8d | 26 | 2.1c | 7 | 1.8 |
| EDHGA5 (weekly) + Ethephon | 23 | 45d | 8.6d | 5.5c | 4.6d | 3.8d | 3.0d | 23 | 2.1c | 2 | 0.8 |
| EDHGA5 (once) + Ethephon | 21 | 67b | 10.2d | 7.8b | 10.6c | 10.6c | 7.5bc | 17 | 4.2b | 4 | 1.0 |
| p value | | 0.0001 | 0.0001 | 0.0001 | 0.0001 | 0.0001 | 0.0001 | | 0.0001 | | 0.4052 |
| LSD(0.05) | | 6 | 2.6 | 1.5 | 1.5 | 2.0 | 0.9 | | 1.1 | | n.s. |

+n = the number of samples taken for each parameters to the right of this number.
EDHGA5 = exo-C-16,17-dihydro GA5

TABLE 2

Tillering and flowering following applications of ethephon and ADHGA5 separately and together to greenhouse grown Bonanza barley.

| Treatment | n+ | Fertile No. | Sterile No. | Early DW g-plant[1] | Tillers Total No. | Late DW g.plant[1] | n | Maturity ZGS | Flowering Florets per Spike Fertile No. | Sterile No. | Spike DW g.treatment[1] |
|---|---|---|---|---|---|---|---|---|---|---|---|
| Control | 20 | 1.4a | 0.7cd | 1.6 | 1.6c | 0.1 | 29 | 90ab | 34ab | 13cd | 36.1 |
| Activator | 23 | 1.1a | 0.5d | 1.4 | 0.3c | 0.0 | 25 | 91a | 42a | 11d | 40.3 |
| Ethephon | 22 | 0.5b | 9.9bcd | 1.0 | 6.5a | 1.3 | 12 | 91a | 21bc | 29b | 10.6 |
| Ethephon + Activator | 24 | 0.5b | 0.6cd | 0.8 | 5.0b | 1.3 | 13 | 91a | 22b | 25bc | 11.4 |
| EDHGA5 (weekly) | 26 | 0.4b | 1.2b | 1.2 | 3.8b | 0.5 | 11 | 87b | 3cd | 50a | 5.2 |
| EDHGA5 (weekly) + Ethephon | 23 | 0.0d | 2.8a | 1.1 | 7.8a | 0.8 | 1 | 91a | 1d | 57a | 0.1 |
| EDHGA5 (once) + Ethephon | 21 | 0.5b | 1.0bc | 1.1 | 7.1a | 1.2 | 13 | 91a | 24b | 29b | 11.1 |
| p value | | 0.0001 | 0.0001 | 0.0001 | | | | 0.0013 | 0.0001 | 0.0001 | |
| LSD(0.05) | | 0.3 | 0.4 | 1.4 | | | | 3 | 18 | 14 | | n = the number of samples taken for each parameter to the right of this number.
EDHGA5 = exo-C-16,17-dihydro GA5

EXAMPLE 16

Mechanism of Action of C-16,17 Dihydro Gas in Retarding The Growth of Higher Plants Stable isotope-labeled [$^2$H2] gibberellin A20 was applied to dwarf rice cv. Tan-ginbozu (100 ng/plant) in the presence and absence of C-16,17 dihydro GA5 (also applied at 100 ng/plant).

The gibberellins noted above were applied in microdrops to the shoot of the young rice plant, and 72 hours later the plant shoots were harvested, and extracted for analysis of [$^2$H2] GA1 levels by gas chromatography-mass spectrometry. Stable isotope-labeled [$^2$H2] GA1 was added as an internal standard in order to quantify the levels of [$^2$H]GA1, which was the major metabolite of the applied $^2$H]GA20.

RESULTS

TABLE I

Height to the Second Leaf Sheath, in mm, of the Rice Plant in Response to Application of Deuterated GA20, or deuterated GA20 + C-16,17 dihydro GA5,

| Treatment | Leaf Sheath Height (Length) |
|---|---|
| A. [$^2$H2] gibberellin A20 applied (100 ng/plant) | 25.25 mm +/− 0.98 (+/− is P = 0.01 confidence range) |
| B. As above in A., but with C-16,17 dihydro GA5 (100 | 18.50 mm +/− 0.76 (+/− is P = 0.01 confidence range) |

TABLE II

Actual Growth of the Rice Plant in Response to Application of Deuterated GA20, or Deuterated GA20 + C-16,17 dihydro GA5, Relative to Control (No GA Applied) Rice Plants, in mm and as a Percentage of Growth (Delta Growth above Control Growth),

| Treatment | Growth Response Rel. to Control |
|---|---|
| A. [$^2$H2] gibberellin A20 applied (100 ng/plant) | 16.45 mm of growth above control = 100% |
| B. As above in A., but with C-16,17-dihydro GA5 (100 ng per plant) | 9.70 mm of growth above control = 41% Growth Reduction |

TABLE III

Amount of [$^2$H2] GA1 present in the Rice Plant When Harvested at Hour 72 After Application to the of the Rice Plant of 100 ng of Deuterated GA20, or of 100 ng of Deuterated GA20 + 100 ng of C-16,17 dihydro GA5,

| Treatment | Picograms of [$^2$H2] GA1 Present per Rice Plant at Hour 72 After Application of [$^2$H2]GA20 |
|---|---|
| A. [$^2$H2] gibberellin A20 | 3.40 pg/rice plant = |

TABLE III-continued

Amount of [²H2] GA1 present in the Rice Plant When Harvested at Hour 72 After Application to the of the Rice Plant of 100 ng of Deuterated GA20, or of 100 ng of Deuterated GA20 + 100 ng of C-16,17 dihydro GA5,

| Treatment | Picograms of [²H2] GA1 Present per Rice Plant at Hour 72 After Application of [²H2]GA20 |
|---|---|
| applied (100 ng/p[lant] | 100% |
| B. As in A. above, but with C-16,17-dihydro GA5 (100 ng | 2.15 pg/rice plant = 37% Reduction in [²H2] GA1 |

Thus, application of 100 ng of C-16,17 dihydro GA5 significantly reduced the growth that should have been effected by application of 100 ng of [²H2] GA20. This retarding effect constituted a 41% reduction in height growth (delta height).

Further, assessment of the level of "effector" gibberellin A1 (e.g. [²H2]GA1) that was extractable from the rice plant 72 hrs after application of [²H2]GA20 showed that the deuterated GA1 levels were reduced by 37%, relative to plants to which only the deuterated GA20 had been applied.

CONCLUSIONS

The proportion by which shoot growth was reduced by application of C-16,17 dihydro GA5 (41% reduction) is almost the same as the proportion by which extractable levels of deuterated GA1 have been reduced (37%).

This evidence, together with evidence shown in Example 4 (see earlier) is indicative that the mechanism of action of C-16,17 dihydro GaaS in retarding shoot growth, at least, is due to a partial blockage of the 3β-hydroxylation step (e.g. GA20——/—>GA1 in the example given for rice) by application of C-16,17 dihydro GA5.

It is also reasonable to conclude that growth retardation, and possibly many other desireable effects brought about by application of C-16,17 dihydro GA5 and other C-16,17 dihydro gibberellins has the same mechanism of action, most notably inhibition of 3β-hydroxylation.

Many higher plant species utilize gibberellin A1 (GA1) or GA3 as "effectors" of shoot growth. A biosynthetic precursor of GA1 or GA3 is gibberellin A10. Gibberellin A20 is thus metabolized to GA1 by 3β-hydroxylation, and to GA3 via GA5, this time by 3β-hydroxylation of GA5.

The evidence of this example is that a dwarf rice plant which has been induced to grow by application of GA20 can have this growth significantly reduced by simultaneous application of C-16,17 dihydro GA5, and that the mechanism of this growth retardation most likely involves an inhibition of the 3β-hydroxylation of GA20—>GA1, the latter gibberellin being the "effector" of shoot elongation.

EXAMPLE 17

Improvement of Fruit Quality—Cherries

Five levels of C-16,17 dihydro GA5 (0, 3.3, 10, 33.3 and 100 ppm) were compared with a similar range of gibberellin A3 levels. Application was made by spraying in aqueous solutin (+surfactant) to drip-off to fruitbearing branch units in late June, 1991.

RESULTS

I. Higher levels of GA3 significantly promoted shoot growth, whereas no level of C-16,17 dihydro GA5 had this undesired effect (see below).

II. Fruit weight at harvest was increased by both GAs , although most effectively by GA3 (data not shown).

III. Fruit colouring was delayed by both GAs, but most effectively by high levels of GA3 (data not shown).

IV. Fruit firmness was improved, and post harvest "pitting" (a physiological disorder) was reduced by both GAs although most effectively by GA3 (see Tables below).

TABLE I

Effects of C-16,17 dihydro GA5 and GA3 on Shoot Elongation of Cherry Branches

Shoot Elongation in cm (values with the same letters do not differ significantly at P = 0.05

| Treatment | No. Branches | Mean Branch Length (cm) |
|---|---|---|
| Gibberellin A3 | | |
| 0 | 21 | 0.690 B,C |
| 3.33 ppm | 22 | 4.091 B |
| 10 ppm | 17 | 0.412 C |
| 33.3 ppm | 23 | 4.065 B |
| 100 ppm | 22 | 8.773 A |
| C-16,17 dihydro GA5 | | |
| 0 | 21 | 0.690 B,C |
| 3.33 ppm | 17 | 0.053 D,C |
| 10 ppm | 22 | 2.175 B,C |
| 33.3 ppm | 10 | 0.580 C |
| 100 ppm | 22 | 0.977 B,C |

CONCLUSIONS

These results with C-16,17 dihydro GA5, although preliminary, are important because they indicate that it may be possible to separate (by using C-16,17 dihydro GAs) the shoot growth promotion that has traditionally been found to occur after GA3 application, from the more desireable effects of increased fruit weight, delaying of fruit colouring, enhanced fruit firmness, and a reduction in fruit pitting that can be brought about by the use of C-16,17 dihydro GA5.

Thus, only 100 ppm GA3 significantly promoted shoot growth, although 33.3 ppm and 3.33 ppm GA3 sprays tended to do so, as did 10 ppm C-16,17 dihydro GA5.

TABLE II

Effects of C-16,17 di-hydro GA5 and GA3 Sprays on Quality (Average Fruit Firmness) of Lambert Cherry Fruit Firmness in Newtons (values with the same letters do not differ significantly at P = 0.05

| Treatment | No. Fruit | Mean Measure of Fruit Quality |
|---|---|---|
| Gibberellin A3 | | |
| 0 | 154 | 70.7143 G |
| 3.33 ppm | 196 | 76.2270 D |
| 10 ppm | 208 | 77.9399 C |
| 33.3 ppm | 172 | 81.6221 A |
| 100 ppm | 223 | 79.8969 B |
| C-16,17 dihydro GA5 | | |

TABLE II-continued

Effects of C-16,17 di-hydro GA5 and GA3 Sprays on
Quality (Average Fruit Firmness) of Lambert Cherry Fruit

| Treatment | No. Fruit | Firmness in Newtons (values with the same letters do not differ significantly at P = 0.05) Mean Measure of Fruit Quality |
| --- | --- | --- |
| 0 | 154 | 70.7143 G |
| 3.33 ppm | 222 | 73.7950 F |
| 10 ppm | 153 | 75.2941 E |
| 33.3 ppm | 158 | 74.1020 F |
| 100 ppm | 172 | 74.5827 E,F |

Although GA3 was most effective in increasing fruit firmness, C-16,17 dihydro GA5 at all levels was significantly better than Controls (0 levels), thereby indicating that a higher dosage may hold promise of even greater fruit firmness, but w/o causing an increase in shoot elongation.

TABLE III

Effects Of C-16,17 dihydro GA5 and GA3 Sprays on
Quality (Average Level of Pitting after a Period of Cold Storage)
of Lambert Cherry Fruit

| Treatment | No. Fruit | Average Pitting Scale* (values with the same letters do not differ significantly at P = 0.05) Mean Measure of Fruit Quality |
| --- | --- | --- |
| Gibberellin A3 | | |
| 0 | 154 | 0.97727 A |
| 3.33 ppm | 196 | 0.75266 D |
| 10 ppm | 208 | 0.68269 D |
| 33.3 ppm | 172 | 0.44767 E |
| 100 ppm | 223 | 0.45516 E |
| C-16,17 dihydro GA5 | | |
| 0 | 154 | 0.97727 A |
| 3.33 ppm | 222 | 0.88964 B,C |
| 10 ppm | 153 | 0.85621 C |
| 33.3 ppm | 158 | 0.94558 A,B |
| 100 ppm | 172 | 0.86047 C |

*Scale = 0–3 where 0 = none, 1 = slight, 2 = moderate, 3 = severe.

Although GA3 was most effective in decreasing fruit pitting, C-16,17 dihydro GA5 at three levels was significantly better than Controls (0 level), thereby indicating that a higher dosage may hold promise of yielding a grater reduction in fruit pitting, but w/o causing an increase in shoot elongation.

We claim:

1. A method for promoting a desired tissue morphology and/or physiological state in a higher plant, wherein said desired tissue morphology or physiological state is selected from at least one of
   (i) dwarfing
   (ii) stem and shoot and/or root (radicle) growth retardation
   (iii) flowering
   (iv) improved fruit quality
   (v) inhibiting fruit ripening
   (vi) improving fruit set
   (vii) controlling weed growth
   (viii) inducing male sterility
   (ix) retarded bud break
   (x) tillering
which comprises applying to the plant an amount of a C-16,17-dihydro gibberellin or C-16,17-dihydro gibberellin precursor effective to promote the desired tissue morphology and/or physiological state in the plant.

2. A method for promoting a desired tissue morphology and/or physiological state in a higher plant, wherein said desired tissue morphology or physiological state is selected from at least one of
   (i) dwarfing
   (ii) stem and shoot and/or root (radicle) growth retardation
   (iii) flowering
   (iv) improved fruit quality
   (v) inhibiting fruit ripening
   (vi) improving fruit set
   (vii) controlling weed growth
   (viii) inducing male sterility
   (ix) retarded bud break
   (x) tillering
which comprises applying to the plant an amount of a C-16,17-dihydro gibberellin or C-16,17-dihydro gibberellin precursor effective to produce an at least partial inhibition of gibberellin 3β-hydroxylase activity in said plant.

3. A method for promoting a desired tissue morphology and/or physiological state in a higher plant wherein said desired tissue morphology or physiological state is selected from at least one of
   (i) dwarfing
   (ii) stem and shoot and/or root (radicle) growth retardation
   (iii) flowering
   (iv) improved fruit quality
   (v) inhibiting fruit ripening
   (vi) improving fruit set
   (vii) controlling weed growth
   (viii) inducing male sterility
   (ix) retarded bud break
   (x) tillering
which comprises applying to the plant an amount of a C-16,17-dihydro gibberellin or a C-16,17-dihydro gibberellin precursor effective to produce at least partial inhibition of the formation of effector gibberellins in said plant.

4. A method for promoting flowering in a higher plant, which comprises applying to the plant an amount of a C-16,17-dihydro gibberellin or C-16,17-dihydro gibberellin precursor effective to promote flowering.

5. A method according to claim 4 wherein flowering is promoted (a) with a simultaneous retardation of stem or shoot elongation or (b) with a nil or negligible effect on stem or shoot elongation.

6. A method for retarding stem or shoot growth in a higher plant, which comprises applying to the plant an amount of a C-16,17-dihydro gibberellin or C-16,17-dihydro gibberellin precursor effective to promote flowering.

7. A method for improving fruit quality in a higher plant, which comprises applying to the plant an effective amount of a C-16,17-dihydro gibberellin or C-16,17-dihydro gibberellin precursor.

8. A method for inhibiting ripening of fruit of a higher plant plant, which comprises applying to the plant an effective amount of a C-16,17-dihydro gibberellin or C-16,17-dihydro gibberellin precursor.

9. A method for improving fruit set in a higher plant, which comprises applying to the plant an effective amount of a C-16,17-dihydro gibberellin or C-16,17-dihydro gibberellin precursor.

10. A method of controlling growth of weeds in an area of land which comprises applying to said land area a C-16,17-dihydro gibberellin or C-16,17-dihydro gibberellin precursor.

11. A method for inducing male sterility in a higher plant, which comprises applying to the plant an effective amount of a C-16,17-dihydro gibberellin or C-16,17-dihydro gibberellin precursor.

12. A method for retarding bud break in a higher plant, which comprises applying to the plant an amount of a C-16,17-dihydro gibberellin or C-16,17-dihydro gibberellin precursor effective to promote flowering.

13. A method for inhibiting formation of effector gibberellins in a plant, which comprises applying to the plant an amount of a C-16,17-dihydro gibberellin or C-16,17-dihydro gibberellin precursor.

14. A method according to claim 1 wherein the C-16,17-dihydro gibberellin or C-16,17-dihydro gibberellin precursor has a formula selected from formulae Ia, Ib, Ic, Id and Ie:

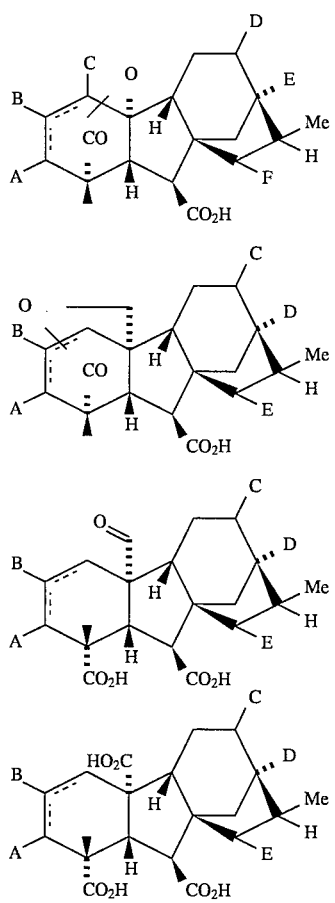

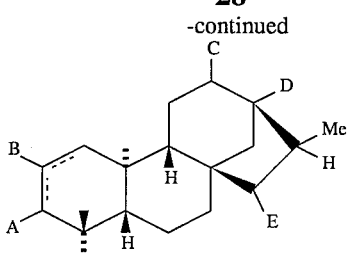

wherein A,B,C,D, E and F independently represent hydrogen atoms or hydroxyl groups and the dotted line represents one optional double bond either between the carbon atoms in positions 1 and 2 or between the carbon atoms in positions 2 and 3.

15. A method according to claim 1 wherein the gibberellin precursor is selected from C-16,17-dihydro steviol, C-16,17-dihydro ent-kaurene, C-16,17-dihydro ent-kaurenoic acid, C-16,17-dihydro- 7-hydroxy kaurenoic acids, C-16,17-dihydro-16,17-dihydroxy kaurenoic acids and C-16,17-dihydro kaurenoic acids.

16. A method according to claim 1 wherein the gibberellin or gibberellin precursor is the C-2,3 dehydro, or C-1,2 dehydro derivative of a C- 16,17-dihydro gibberellin or a C-16,17-dihydro gibberellin precursor.

17. A method according to claim 1 wherein the C-16,17-dihydro gibberellin or C-16,17-dihydro gibberellin precursor has a hydroxy substituent in the 17-position.

18. A method according to claim 1 wherein the C-16,17-dihydro gibberellin or C-16,17-dihydro gibberellin precursor has a hydroxy substituent in both the 16- and the 17-positions.

19. A method according to claim 1 wherein the C-16,17-dihydro gibberellin or C-16,17-dihydro gibberellin precursor has the hydroxylation pattern and stereochemical structure of GA5.

20. A method according to claim 14 wherein said C-16,17-dihydro gibberellin is selected from C-16,17-dihydro gibberellin $A_3$ and C-16,17-dihydro gibberellin $A_5$.

21. A method according to claim 1 wherein said gibberellin is selected from:

C-16.17-dihydro $GA_3$;
C-16,17-dihydro $GA_{20}$;
C-16,17-dihydro,2,3 didehydro $GA_9$;
C-16,17-dihydro,1,2 didehydro $GA_9$;
C-16,17-dihydro $GA_{12}$;
C-16,17-dihydro $GA_{15}$;
C-16,17-dihydro $GA_{53}$;
the C-2,3dehydro derivative of C-16,17-dihydro $GA_{12}$;
the C-2,3dehydro derivative of C-16,17-dihydro $GA_{15}$;
the C-2,3dehydro derivative of C-16,17-dihydro $GA_{53}$;
the C-1,2-dehydro derivative of C-16,17-dihydro $GA_{20}$;
the C-1,2-dehydro derivative of C-16,17-dihydro $GA_{12}$;
the C-1,2-dehydro derivative of C-16,17-dihydro $GA_{15}$; and
the C-1,2-dehydro derivative of C-16,17-dihydro $GA_{53}$.

22. A method according to claim 20 wherein said gibberellin is C-16,17-dihydro $GA_5$.

23. A method according to claim 1 wherein said C-16,17-dihydro gibberellin or gibberellin precursor is applied in the form of a free acid or salts or esters thereof.

24. A method according to claim 23 wherein said salts and esters are selected from sodium and potassium salts and the $C_{1-4}$ carboxylic acid esters.

25. A method according to claim 1 wherein said C-16, 17-dihydro gibberellin or gibberellin precursor is applied together with another plant growth regulators.

26. A method according to claim 1 wherein said C-16, 17-dihydro gibberellin or gibberellin precursor is applied by spraying a solution or suspension thereof to whole plants, or by seed application, together with a suitable carrier.

27. A method according to claim 1 wherein said C-16, 17-dihydro gibberellin or gibberellin precursor is applied at a rate of from 2 to 100 micrograms per gram fresh weight of actively growing plant tissue.

28. A method according to claim 1 wherein said C-16, 17-dihydro gibberellin or gibberellin precursor is applied at a concentrations of from 2–600 ppm, preferably from 5–450 ppm.

29. A method according to claim 1 wherein the plant species is a floriculturally, agronomically, or horticulturally useful monocot or dicot, or gymnosperm, including woody ornamental or fruiting shrubs, or woody ornamental or fruiting trees, or a conifer of the Gymnospermae Order.

30. A method according to claim 1 wherein the C-16,17-dihydro gibberellin or C-16,17-dihydro gibberellin precursor is applied prior to natural floral initiation.

31. A method according to claim 1 wherein the C-16,17-dihydro gibberellin or C-16,17-dihydro gibberellin precursor is applied after natural floral initiation, but during early stages of floral differentiation.

32. A method according to claim 1 wherein the C-16,17-dihydro gibberellin or C-16,17-dihydro gibberellin precursor is applied during early stages of floral development.

33. A method according to claim 1 wherein the C-16,17-dihydro gibberellin or C-16,17-dihydro gibberellin precursor is applied to dry, imbibed or imbibing seeds so as to ovecome a natural requirement for low temperature, particularly to obviate vernalization).

34. A method according to claim 1 wherein the plant species is a member of the Gramineae.

35. A method according to claim 34 wherein the plant species is wheat or barley.

36. A method according to claim 1 wherein the plant species is oilseed rape.

37. A method according to claim 1 wherein the plant species is a member of the Araceae.

38. A method according to claim 1 wherein the plant species is any monocotyledenous or dicotyledenous plant with a natural requirement for cold to promote flowering.

39. A method according to claim 1 wherein the gibberellin is applied as a seed soak in an appropriate aqueous or organic solution yielding an uptake by the seed of from 1 picogram to 10 micrograms per seed.

40. A method according to claim 1 wherein the gibberellin is applied at a rate of 10 nanograms to 100 milligrams per plant for herbaceous plants (the effective dose depending on species and size of plant), 10 micrograms to 500 milligrams per plant for shrubs, and at a rate of 1 milligram to 20 grams per plant for trees.

41. A method according to claim 1 wherein the gibberellin is at a concentration up to 5000 ppm.

42. A method according to claim 1 wherein the gibberellin is at a concentration of from 1 to 3000 ppm.

43. A method according to claim 1 wherein the gibberellin is at a concentration in the range from 1–1000 ppm.

44. A method according to claim 1 wherein the gibberellin is applied at a concentration in the range from 5–1000 ppm as a foliar spray and/or as a soil drench.

45. A method according to claim 1 wherein the gibberellin is applied at a concentration in the range from 5–350 ppm as a foliar spray and/or as a soil drench.

46. A method according to claim 1 wherein the gibberellin is applied as a seed soak at a concentration in the range of $10^{-12}$ to $1.5 \times 10^{-2}$ molar.

47. A method according to claim 1 wherein the gibberellin is applied as a seed soak at a concentration in the range of $10^{-12}$ to $10^{-7}$ molar.

48. A method according to claim 1 wherein the gibberellin is applied at a rate of up to 1000 micrograms/gram fresh weight.

49. A method according to claim 1 wherein the gibberellin is applied at a rate of from 1 to 1000 micrograms/gram fresh weight.

50. A method according to claim 1 wherein the gibberellin is applied at a rate of from 2 to 1000 micrograms/gram fresh weight.

51. A method according to claim 1 wherein the gibberellin is applied at a rate of from 2 to 500 micrograms/gram fresh weight.

52. A method according to claim 1 wherein the gibberellin is applied at a rate of from 2 to 333 micrograms/gram fresh weight.

53. A method according to claim 1 wherein the gibberellin is applied at a rate of from 2 to 100 micrograms/gram fresh weight.

54. A composition comprising an amount of C-16,17-dihydro gibberellin or C-16,17-dihydro gibberellin precursor effective to promote, in a higher plant, a desired tissue morphology and/or physiological state selected from at least one of (i) dwarfing (ii) stem and shoot and/or root (radicle) growth retardation (iii) flowering (iv) improved fruit quality (v) inhibiting fruit ripening (vi) improving fruit set (vii) controlling weed growth (viii) inducing male sterility (ix) retarded bud break (x) tillering, together with an agriculturally or horticulturally acceptable diluent or carrier.

55. A composition according to claim 54, wherein said composition is substantially free of gibberellins which are C- 16,17-dehydro.

56. A composition according to claim 54, wherein the C-16,17-dihydro gibberellin or C-16,17-dihydro gibberellin precursor is as defined in any one of claims 14 to 24.

57. A composition according to claim 54, wherein said gibberellin or gibberellin precursor is contained in a concentration of up to 5,000 ppm.

58. A composition according to claim 54, wherein said gibberellin or gibberellin precursor is contained in a concentration of from 1 to 3,000 ppm.

59. A composition according to claim 54, wherein said gibberellin or gibberellin precursor contained in a concentration of from 1 to 1,000 ppm.

* * * * *